United States Patent
Berka et al.

(10) Patent No.: US 6,682,922 B2
(45) Date of Patent: Jan. 27, 2004

(54) POLYPEPTIDES HAVING PHOSPHOLIPASE ACTIVITY AND NUCLEIC ACIDS ENCODING SAME

(75) Inventors: Randy M. Berka, Davis, CA (US); Michael W. Rey, Davis, CA (US); Tony Byun, Rohnert Park, CA (US); Ryoko Itami, Sukagawa (JP); Noriko Tsutsumi, Ichikawa (JP); Alan Klotz, Indianapolis, IN (US)

(73) Assignees: Novozymes Biotech, Inc., Davis, CA (US); Novozymes Bioindustry, Ltd., Chiba (JP)

( * ) Notice: Subject to any disclaimer, the term of this patent is extended or adjusted under 35 U.S.C. 154(b) by 0 days.

(21) Appl. No.: 10/263,250

(22) Filed: Oct. 2, 2002

(65) Prior Publication Data

US 2003/0100092 A1 May 29, 2003

Related U.S. Application Data

(60) Division of application No. 09/437,687, filed on Nov. 10, 1999, now Pat. No. 6,489,154, which is a continuation-in-part of application No. 09/189,486, filed on Nov. 10, 1998, now abandoned.

(51) Int. Cl.[7] .............................. C12N 9/20; C12N 1/20; C12N 15/00; C07K 1/00; C07H 21/04
(52) U.S. Cl. ................. 435/198; 435/252.3; 435/320.1; 530/350; 536/23.2
(58) Field of Search ............................. 435/198, 252.3, 435/320.1; 536/23.2; 530/350

(56) References Cited

FOREIGN PATENT DOCUMENTS

| | | |
|---|---|---|
| JP | 10155493 | 6/1998 |
| WO | WO 98/26057 | 6/1998 |

OTHER PUBLICATIONS

Saito et al., 1991, Methods in Enzymology 197: 446–456.
Chen et al., 1997, Infection & Immunity 65: 405–411.
Fifis et al., 1996, Veterinary Microbiology 49: 219–233.
Kawaski, 1975, Journal of Biochemistry 77: 1233–1244.
Masuda et al., 1991, European Journal of Biochemistry 202: 783–787.
Mustranta et al., 1995, Process Biochemistry 30: 393–401.
Ichimasa et al., 1985, Agric. Biol. Chem. 49: 1083–1089.
Lee et al., 1994, Journal of Biological Chemistry 269: 19725–19730.
Kuwabara, 1998, Agric. Biol. Chem. 52: 2451–2458.
Watanabe et al., 1994, FEMS Microbiological Letters 124: 29–34.
Oishi et al., 1996, Biosci. Biotech. Biochem. 60:1087–1092.
Chakravarti et al., 1981, Archives of Biochemistry & Biophysics 206: 393–402.
Uehara et al., 1979, Agric. Biol. Chem. 43: 517–525.

Primary Examiner—Tekchand Saidha
(74) Attorney, Agent, or Firm—Robert L. Starnes

(57) ABSTRACT

The present invention relates to isolated polypeptides having lysophospholipase activity and isolated nucleic acid sequences encoding the polypeptides. The invention also relates to nucleic acid constructs, vectors, and host cells comprising the nucleic acid sequences as well as methods for producing and using the polypeptides.

15 Claims, 10 Drawing Sheets

```
TCTACACCTACTTGAATAGCTATATTCCCCGACATTTATCAGCAATATTCAAGACATTCATATCAATACTTAGACATTG   80

GCTTGTTTCAACAAGCAACATGCTTGGCCCCTCTCGTCTTTACTTTATGGCTTACCAGCTCGGCCATTGTGCCCGGATG  160
                  M   L   G   P   L   V   F   T   L   W   L   T   S   A   I   A   A   P   D

ACGCGGGTTTGGTCGCAGCACCAGCAATTGGCAAATCCCTCAGTATCCCGGACTCTCCAAGCGGCGGTTAT          240
 D   A   G   L   V   A   A   P   A   I   G   K   S   L   S   I   R   A   L   P   D   S   P   S   G   G   Y

GCGCCAAAAGTGGTTGACTGTCCCTGACGCGCCCGAAAATCCGACTTGCCGATGGACTTTCAGACCAGGAAGAAGCCTG  320
 A   P   K   V   V   D   C   P   S   T   R   P   K   I   R   L   A   D   G   L   S   D   Q   E   E   A   W

GGTTCGTCGCCGAAGAAACAACACAATAGATCCAATGAAAGACTTGTTATCCCGAGTCAACATCTCGGGTTTCGACGCCG  400
 V   R   R   R   R   N   N   T   I   D   P   M   K   D   L   L   S   R   V   N   I   S   G   F   D   A

AAAAGTGGATTGAGAAACAAAACAAAAACAATGCGACTCTGCGCTACCTAAACATCGCCATCGCAGCTTCTGGTGGTGGATACCGA  480
 E   K   W   I   E   K   N   K   N   N   A   T   A   L   P   N   I   A   I   A   A   S   G   G   G   Y   R

GCCCTCATGAACGGAGCAGGCTTCATCTCTGCGGCTGACTCACGCAACAACGAATCGGTCCCATCAGTGTCTTCTACA  560
 A   L   M   N   G   A   G   F   I   S   A   A   D   S   R   N   N   E   S   G   P   I   S   G   L   L   Q

ATCTTCCACTTATTTGGCTGGTCTGTCAGGAGGTGGTTGGCTTGGCTCTATCTTTGCCAACAACTTCACCACAATCC   640
 S   T   Y   L   A   G   L   S   G   G   G   W   L   V   G   S   I   F   A   N   N   F   T   T   I

CCGACCTACAAAAGGGAGACAAGGGTTCAGATATCTGGGCTTTTGACCGTTCAATTTTCAAAGGACCCGAAAAGTCAGGC  720
 P   D   L   Q   K   G   D   K   G   S   D   I   W   A   F   D   R   S   I   F   K   G   P   E   K   S   G

TTGAACGTTTTGAACACGGCTAAATACTGGGATGACATAAAGACACCGTTGACGAAAAGGCCGATGGGTGGAATACTAC   800
 L   N   V   L   N   T   A   K   Y   W   D   D   I   K   D   T   V   D   E   K   A   D   G   W   N   T   T
```

Fig. 1A

```
ACTCACTGACTGGTGGGTCGTGCTCTCTGTCTTACCAGCTGATCGATGCCTCTGAGGGTGGTCCTGCTATACTTTCCT  880
 L   T   D   W   G   R   A   L   S   Y   Q   L   I   D   A   S   E   G   G   P   A   Y   T   F   S

CCATCGCCGATACTTCAAGGACGCCGATACCCCATTCCTATCCTCGTTGCCGATGGTCGTGCTCCTGGTCAA  960
 S   I   A   D   T   S   N   F   K   D   A   D   T   P   F   P   I   L   V   A   D   G   R   A   P   G   Q

CGCATCGTTCACTCAACGCAACTGTGTACGAGTTCAACCCGTTCGAGTTCGGAACATGGGATCCCACTAGTTACGGGTT 1040
 R   I   V   S   L   N   A   T   V   Y   E   F   N   P   F   E   F   G   T   W   D   P   T   S   Y   G   F

TGCTCCCGTCGAGTACATCGGCTCTAACTTCACGAATGGAACTATCGAAAAGGGCGGCGAATGTGTACGTGGCTTTGATC 1120
 A   P   V   E   Y   I   G   S   N   F   T   N   G   T   I   E   K   G   G   E   C   V   R   G   F   D

AGTTCGGCTTTGTTATGGGCACATCCTCCCTGTTATTCAACCAGTTCCTGCTCAACAACATCACCAAGATTGGAGAAGAA 1200
 Q   F   G   F   V   M   G   T   S   S   L   F   N   Q   F   L   N   N   I   T   K   I   G   E   E

AATGACATTCCTTCACTTGTCGTGAAGGCTATCCAGGGATTCCTGGTAGCTTTGGATACCAATGATGAGGACATTGCCGA 1280
 N   D   I   P   S   L   V   V   K   A   I   Q   G   F   L   V   A   L   D   T   N   D   E   D   I   A   D

TTATTCTCCCAACCCATTCTACCAGTGGAACGTGACAGGAAAAAGCTACAACGCCAAGGACCATCAATTGACTCTTGTCG 1360
 Y   S   P   N   P   F   Y   Q   W   N   V   T   G   K   S   Y   N   A   K   D   H   Q   L   T   L   V

ACGGAGGGGAGGATCTGCAGAATATCCCACTCCATCCCTTGATCCAGCCTGTTCGTGGTGTGGACATCATCTTTGCCATC 1440
 D   G   G   E   D   L   Q   N   I   P   L   H   P   L   I   Q   P   V   R   G   V   D   I   I   F   A   I

GATTCTTCAGCGGATACGGATAACAACAATTGGCCCAATGGTACCGCTCTTCGTGCGACATACGATCGTGTCGATTCCAGCTT 1520
 D   S   S   A   D   T   D   N   N   W   P   N   G   T   A   L   R   A   T   Y   D   R   V   D   S   S   L

AGGAAACGGAACTCAGTTCCCTCTATTCCATCAGCTGAGACTTTCATTAATGAGAAGTTGAACCAACGCCCAACACTCT 1600
 G   N   G   T   Q   F   P   P   S   I   P   S   A   E   T   F   I   N   E   K   L   N   Q   R   P   T   L
```

Fig. 1B

```
TTGGCTGTGTGATGCAGACAACTTCACGCTTTCAGACGGCAAAGCTCCTCCTCTTGTCTTTCTACATTCCCAACGCGCCC 1680
 F  G  C  D  A  D  N  F  T  L  S  D  G  K  A  P  P  P  L  V  F  Y  I  P  N  A  P

TACACATTCTTGAGCAATGTGTCTCTACCTTCGATCTCTCATACAGCATCCCTGAGCGTGACAGTATCATTCTCAATGCTCT 1760
 Y  T  F  L  S  N  V  S  T  F  D  L  S  Y  S  I  P  E  R  D  S  I  I  L  N  A  L

GAACGGGTGCCACTCAGGGCAATGGTACTATTGATAAGGAATGGCCCATCATGAGCCGAAGTT 1840
 N  G  A  T  Q  G  N  G  T  I  D  K  E  W  P  T  C  V  V  C  A  I  M  S  R  S

GGTGGAAGTCCAATGAGACTGTTCCCAAAGAGTGCAGTACGTGTTTGACAGATACTGCTGGGACGGAAAGTCGAATAAC 1920
 W  W  K  S  N  E  T  V  P  K  E  C  S  T  C  F  D  R  Y  C  W  D  G  K  S  N  N

ACAGCTGTTAAGACTTACGAGCCTGGATTTATCATTGCTAACGAGACTGCGGCGGCGGAAGACAATGCAGCCGTTGCCGG 2000
 T  A  V  K  T  Y  E  P  G  F  I  I  A  N  E  T  A  A  A  E  D  N  A  A  V  A  G

TTTCACCGAGTTGGTATATGTCTGTGTTTGTTGGAGTGGCTTTATTCTTGCTATTCGTAATTAGCATGTAGTTTCT 2080
 F  T  P  S  W  Y  M  S  V  F  V  G  V  A  L  F  L  A  I  S

GAGTTTGAATATATCTACATCATGCCAATAATATAATTAAAAAAAAAAAAAAAAAAA 2141
```

Fig. 1C

```
            M   L   G     F   V   A   L     T   L   W     L   S   T     A   I   A   A     P   E   D
   1    ATGCTCGGTT TTGTGGCCTT GACGCTCTGG CTCAGCACAG CCATTGCCGC TCCGGAAGAC
            T   A   L     I   P   R   V     N   S   V     E   I   R     A   L   P   N     S   P   S
  61    ACGGCTTTGA TCCCCAGGGT CAATTCAGTC GAGATCCGAG CCCTACCAAA TTCTCCGAGT
            G   G   Y     A   P   K   V     V   D   C     P   S   T     R   P   K   A     R   L   A
 121    GGCGGATATG CTCCGAAAGT AGTCGATTGC CCTTCAACAC GTCCAAAAGC TCGTCTTGCC
            D   G   L     S   S   E   E     E   S   W     V   R   R     R   R   N   N     T   I   D
 181    GATGGACTGT CTAGCGAGGA AGAATCCTGG GTTCGTCGTC GCAGAAACAA CACAATAGAT
            D   L   K     T   F   L   S     R   A   N     I   S   G     F   D   A   E     S   F   V
 241    GACCTAAAGA CATTCTTGTC GCGAGCCAAC ATTTCCGGCT TCGATGCCGA GAGCTTCGTT
            E   K   H     K   N   N   A     T   G   L     P   N   I     A   I   A   A     G   G   G
 301    GAGAAGCATA AAAACAATGC GACTGGTCTA CCCAACATCG CCATCGCCGC GTCCGGCGGT
            G   Y   R     A   L   M   N     G   A   G     F   L   S     A   A   D   S     R   N   N
 361    GGTTATCGCG CTTTGATGAA CGGTGCAGGC TTTCTCTCAG CTGCTGATTC ACGCAACAAC
            K   T   G     P   I   S   G     L   L   Q     S   A   T     Y   L   A   G     L   S   G
 421    AAGACCGGCC CCATCAGCGG CCTTCTCCAG TCAGCAACGT ATCTAGCTGG TCTTTCTGGC
            G   W     L   V   G   S     I   F   A     N   N   F     S   T   V   P     D   L   Q
 481    GGTGGCTGGC TCGTTGGTTC TATTTTCGCC AACAATTTCT CAACAGTGCC AGACTTGCAA
            S   G   D     K   V   W   R     F   D   R     S   I   F     K   G   P   K     S   S   G
 541    TCTGGTGACA AAGTCTGGCG ATTTGATCGC TCCATCTTCA AGGGCCCCAA GAGCTCTGGA
            I   S   L     L   N   T   A     E   Y   W     D   E   M     K   D   A   V     D   D   K
 601    ATCAGTCTCC TCAACACTGC CGAGTACTGG GATGAGATGA AAGATGCCGT TGACGACAAG
            D   K   G     W   N   T   T     L   T   D     W   W   G     R   A   L   S     Y   Q   L
 661    GACAAGGGCT GGAATACTAC TCTCACTGAT TGGTGGGGCC GCGCATTGTC GTATCAGCTC
            V   N   A     P   E   G   G     P   S   Y     T   F   S     S   I   A   D     T   S   N
 721    GTCAATGCGC CTGAGGGTGG ACCTTCATAC ACTTTCTCTT CCATTGCCGA TACCTCCAAC
            F   K   D     A   D   T   P     F   P   I     L   V   A     D   G   R   A     P   G   E
 781    TTCAAGGACG CAGACACACC CTTCCCCATC CTCGTTGCTG ATGGTCGTGC TCCAGGTGAG
```

Fig. 6A

```
          R   V   I   S   L   N   A   T   V   Y   E   F   N   P   Y   E   F   G   T   W
 841  CGGTCATCT CCCTGAATGC TACTGTATAC GAGTTCAACC CATACGAGTT CGGTACATGG
          D   P   T   T   F   G   F   V   P   T   E   Y   L   A   S   N   F   T   N   G
 901  GATCCTACAA CCTTTGGCTT CGTACCCACT GAGTATCTCG CTTCCAACTT CACCAACGGC
          S   I   S   S   K   G   E   C   V   R   G   F   D   Q   I   G   F   V   M   G
 961  AGCATCAGCT CCAAGGGCGA ATGCGTTCGT GGCTTTGATC AGATCGGCTT TGTTATGGGA
          T   S   S   L   F   N   Q   F   L   L   N   N   I   T   K   V   G   K   E
1021  ACATCCTCTT CACTATTCAA CCAGTTCCTT CTCAACAACA TCACCAAGGT CGGCAAAGAG
          N   D   I   P   D   I   V   K   A   I   E   G   V   L   V   G   L   D   E
1081  AATGATATTC CCGACATTGT TGTCAAAGCC ATTGAAGGCG TCTTGGTTGG CTTGGACGAG
          D   D   E   D   I   A   Q   Y   A   P   N   P   F   G   W   N   P   T   D
1141  GATGATGAGG ATATCGCCCA GTATGCACCC AACCCCTTCT TCGGATGGAA CCCTACCGAT
          K   S   V   N   S   K   D   R   Q   L   T   L   V   D   G   G   E   D   L   Q
1201  AAGAGCGTCA ATTCCAAGGA CCGCCAGTTG ACTCTTGTCG ATGGTGGAGA GGATCTGCAG
          N   I   P   L   H   P   L   I   Q   P   V   R   G   V   D   I   I   F   A   I
1261  AACATTCCTC TTCACCCATT GATCCAGCCC GTTCGTGGCG TTGACATCAT TTTTGCCATT
          D   S   A   D   T   D   N   N   W   P   N   G   T   A   L   R   A   T   Y
1321  GATTCGTCTG CTGATACGGA CAACAACTGG CCCAATGGTA CTGCTCTTCG TGCTACATAT
          D   R   V   G   S   S   I   G   N   G   T   L   F   P   S   V   P   S   A   E
1381  GACCGTGTTG GTTCCAGCAT TGGCAACGGC ACACTATTTC CCTCAGTCCC ATCAGCTGAG
          T   F   I   N   E   K   L   N   Q   R   P   T   L   F   G   C   N   A   N   N
1441  ACCTTTATCA ACGAGAAGTT GAACCAGCGC CCTACGCTCT TTGGCTGTAA CGCGAACAAC
          F   T   L   S   D   G   E   V   P   P   L   I   L   Y   I   P   N   A   P
1501  TTCACTCTTT CAGACGGGGA AGTTCCCCCT CCGCTGATCT TGTACATCCC CAACGCTCCC
          Y   T   Y   H   S   N   V   S   T   F   D   M   S   Y   T   T   T   E   R   D
1561  TACACCTACC ACAGTAACGT CTCCACCTTC GACATGTCGT ATACCACTAC CGAACGCGAC
```

Fig. 6B

```
              N  I  I     L  N  A  L     N  G  A     T  Q  G     N  A  T  I     D  K  E
1621    AACATCATTC TTAATGCTCT CAATGGAGCT ACTCAGGGTA ACGCTACCAT TGACAAGGAG
              W  P  T     C  V  A  C     A  V  M     S  R  S     W  K  A     N  E  A
1681    TGGCCTACTT GCGTGGGCGTG TGCTGTCATG AGCAGAAGCT GGTGGAAGGC GAATGAGGCT
              V  P  D     A  C  K  T     C  F  D     R  Y  C     W  D  G  K     S  N  N
1741    GTTCCTGACG CATGCAAGAC CTGCTTCGAT CGCTACTGCT GGGATGGAAA GTCTAACAAC
              T  A  V     K  S  Y  E     P  E  Y     I  I  G     G  N  A  T     A  E  A
1801    ACTGCTGTCA AGAGCTATGA GCCCGAGTAC ATCATTGGAG GAAATGCGAC CGCGGAAGCC
              A  D  N     A  A  G  A     R  L  G     P  S  W     F  V  S  A     G  V  G
1861    GCAGACAACG CTGCTGGAGC CAGGCTTGGT CCAAGCTGGT TTGTATCGGC TGGTGTCGGG
              A  A  A     L  F  A  L     M  *
1921    GCGGCTGCTT TGTTTGCTCT CATGTGA
```

Fig. 6C ic acid sequences encoding the polypeptides. The invention also relates to nucleic acid constructs, vectors, and host cells comprising the nucleic acid sequences as well as methods for producing and using the polypeptides.

POLYPEPTIDES HAVING PHOSPHOLIPASE ACTIVITY AND NUCLEIC ACIDS ENCODING SAME

CROSS-REFERENCE TO RELATED APPLICATION

This application is a divisional of pending U.S. application Ser. No. 09/437,687 filed on Nov. 10, 1999, now U.S. Pat. No. 6,489,154, which is a continuation-in-part of U.S. application Ser. No. 09/189,486 filed on Nov. 10, 1998, now abandoned, which are fully incorporated herein by reference.

BACKGROUND OF THE INVENTION

1. Field of the Invention

The present invention relates to isolated polypeptides having lysophospholipase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Phospholipases are enzymes that participate in the hydrolysis of phospholipids which consist of a glycerol backbone with two fatty acids in an outer (sn-1) and the middle (sn-2) positions and esterified with phosphoric acid in the third position. The phosphoric acid may, in turn, be esterified to an amino alcohol.

Several types of phospholipase activity can be distinguished which hydrolyze the fatty acyl moieties. Phospholipase A1 and A2 catalyze the deacylation of one fatty acyl group in the sn-1 and sn-2 positions, respectively, from a diacylglycerophospholipid to produce lysophospholipid. Lysophospholipase (also called phospholipase B by the Nomenclature Committee of the International Union of Biochemistry on the Nomenclature and Classification of Enzymes {Enzyme Nomenclature, Academic Press, New York, 1992}) catalyzes the hydrolysis of the remaining fatty acyl group in a lysophospholipid. A phospholipase B has been reported from *Penicillium notatum* (Saito et al., 1991, *Methods in Enzymology* 197:446–456) which catalyzes the deacylation of both fatty acids from a diacylglycerophospholipid and intrinsicly possesses lysophospholipase activity.

Fungal enzymes with phospholipase activity have been reported from various sources, including *Cryptococcus neoformans* (Chen et al., *Infection and Immunity* 65: 405–411), *Fusobacterium necrophorum* (Fifis et al., 1996, *Veterinary Microbiology* 49: 219–233), *Penicillium notatum* (also known as *Penicillium chrysogenum;* Kawasaki, 1975, *Journal of Biochemistry* 77: 1233–1244; Masuda et al., 1991, *European Journal of Biochemistry* 202: 783–787), *Penicillium cyclopium* (Mustranta et al., 1995, *Process Biochemistry* 30: 393–401), *Saccharomyces cerevisia* (Ichimasa et al., 1985, *Agric. Biol. Chem.* 49: 1083–1089; Paultauf et al., 1994, *Journal of Biological Chemistry* 269: 19725–19730), *Torulaspora delbrueckii* (old name *Saccharomyces rosei,* Kuwabara, 1988, *Agric. Biol. Chem.* 52: 2451–2458; Watanabe et al., 1994, *FEMS Microbiological Letters* 124: 29–34), *Schizosaccharomyces pombe* (Oishi et al., 1996, *Biosci. Biotech. Biochem.* 60: 1087–1092), *Neurospora crassa* (Chakravarti et al., 1981, *Archives of Biochemistry and Biophysics* 206: 393–402), *Aspergillus niger* (Technical Bulletin, G-zyme™ G6999, Enzyme Bio-Systems Ltd.; Mustranta et al., 1995, supra), *Corticium centrifugum* (Uehara et al., 1979, *Agric. Biol. Chem.* 43: 517–525), *Fusarium oxysporum* (WO 98/26057), and *Fusarium solani* (Tsung-Che et al., 1968, *Phytopathological Notes* 58:1437–38).

Fungal phospholipase genes have been cloned from several sources including *Penicillum notatum* (Masuda et al., 1991, supra), *Torulaspora delbrueckii* (Watanabe et al., 1994, *FEMS Microbiology Letters* 124: 29–34), *Saccharomyces cerevisiae* (Lee at al., 1994, *Journal of Biological Chemistry* 269: 19725–19730), Aspergillus (JP 10155493), *Neurospora crassa* (EMBL 042791), and *Schizosaccharomyces pombe* (EMBL 013857).

It is an object of the present invention to provide improved polypeptides having lysophospholipase activity and nucleic acid encoding the polypeptides.

SUMMARY OF THE INVENTION

The present invention relates to isolated polypeptides having lysophospholipase activity selected from the group consisting of:

(a) a polypeptide having an amino acid sequence which has at least 65% identity with amino acids 38 to 654 of SEQ ID NO. 2 or amino acids 17 to 648 of SEQ ID NO. 16;

(b) a polypeptide encoded by a nucleic acid sequence which hybridizes under high stringency conditions with (i) nucleotides 214 to 2061 of SEQ ID NO. 1 or nucleotides 49 to 1944 of SEQ ID NO. 15; (ii) the genomic DNA sequence containing nucleotides 214 to 2061 of SEQ ID NO. 1 or nucleotides 49 to 1944 of SEQ ID NO. 15; (iii) a subsequence of (i) or (ii) of at least 100 nucleotides; or (iv) a complementary strand of (i), (ii), or (iii);

(c) an allelic variant of (a) or (b); and (d) a fragment of (a), (b) or (c), wherein the fragment has lysophospholipase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIGS. 1A, 1B, and 1C show the cDNA sequence and the deduced amino acid sequence of a *Fusarium venenatum* lysophospholipase (SEQ ID NOS. 1 and 2, respectively).

FIGS. 6A, 6B, and 6C show the cDNA sequence and the deduced amino acid sequence of a *Fusarium verticillioides* lysophospholipase (SEQ ID NOS. 15 and 16, respectively).

DETAILED DESCRIPTION OF THE INVENTION

Polypeptides Having Lysophospholipase Activity

Figure 2:
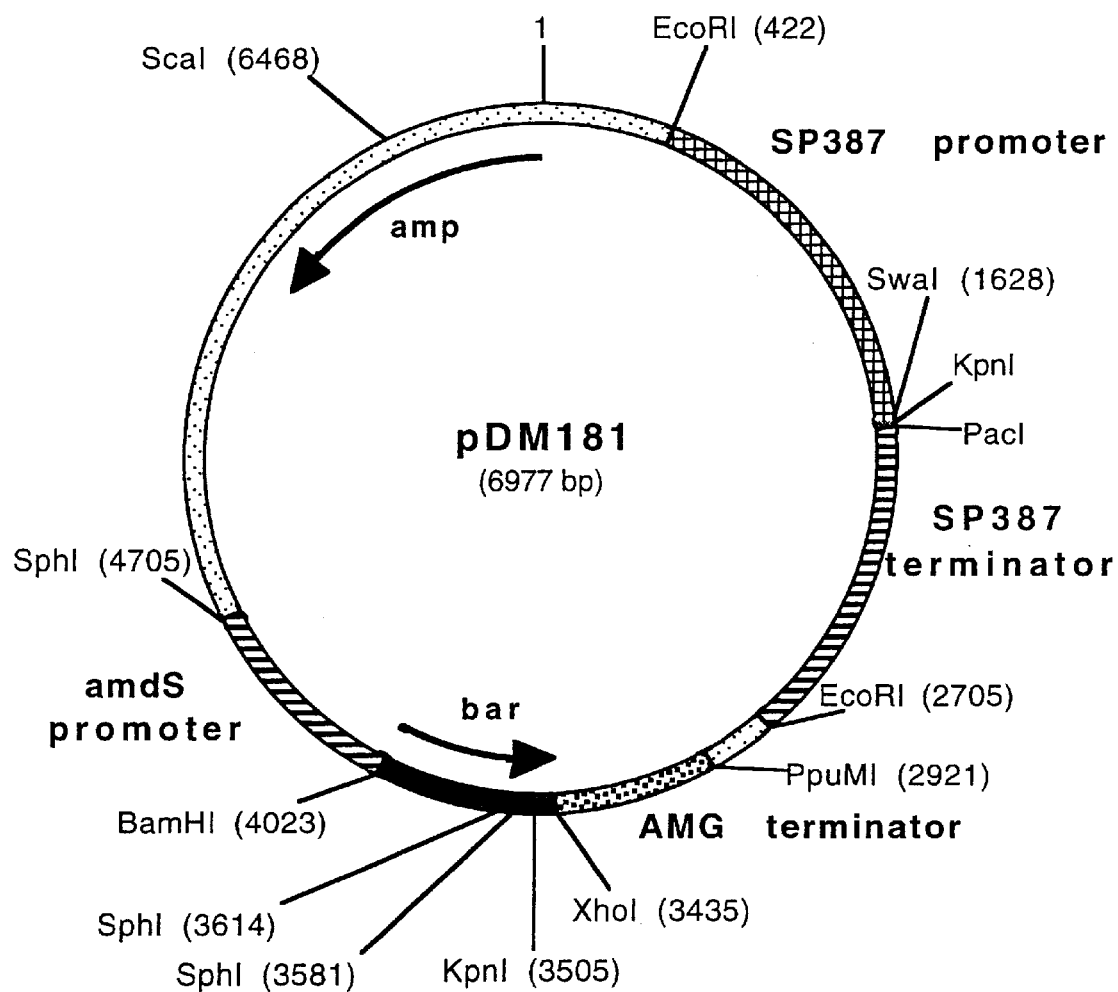
FIG. 2 shows a restriction map of pDM 181.

The term "lysophospholipase activity" is defined herein as a carboxylic ester hydrolysis activity which catalyzes the deacylation of one or both of the fatty acyl groups in the sn-i and sn-2 positions of a diacylglycerophospholipid. For purposes of the present invention, lysophospholipase activity is determined by incubating the lysophospholipase with lysolecithin (or L-α-lysophosphatidylcholine) in the presence of calcium chloride at 37° C., pH 5 or 7 for 10 minutes and measuring the release of fatty acid using any method known in the art such as the NEFA C assay kit (Wako Chemicals, Richmond, Va.) according to the manufacturer's instructions. One unit of lysophospholipase activity is defined as 1.0 μmole of free fatty acid produced per minute at 37° C., ph 5.0 or pH 7.0.

In a first embodiment, the present invention relates to isolated polypeptides having an amino acid sequence which has a degree of identity to amino acids 38 to 654 of SEQ ID NO. 2 or amino acids 17 to 648 of SEQ ID NO. 16, of at least about 65%, preferably at least about 70%, more preferably at least about 80%, even more preferably at least about 90%, most preferably at least about 95%, and even most preferably at least about 97%, which have lysophospholipase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 38 to 654 of SEQ ID NO. 2 or amino acids 17 to 648 of SEQ ID NO. 16. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO. 2 or an allelic variant thereof; or a fragment thereof that has lysophospholipase activity. In a more preferred embodiment, the polypeptide of the present invention comprise the amino acid sequence of SEQ ID NO. 2. In another preferred embodiment, the polypeptide of the present invention comprises amino acids 38 to 654 of SEQ ID NO. 2, which is the mature polypeptide of SEQ ID NO. 2, or an allelic variant thereof; or a fragment thereof, wherein the fragment has lysophospholipase activity. In another preferred embodiment, the polypeptide of the present invention comprises amino acids 38 to 654 of SEQ ID NO. 2. In another preferred embodiment, the polypeptide of the present invention consists of the amino acid sequence of SEQ ID NO. 2 or an allelic variant thereof; or a fragment thereof, wherein the fragment has lysophospholipase activity. In another preferred embodiment, the polypeptide of the present invention consists of the amino acid sequence of SEQ ID NO. 2. In another preferred embodiment, the polypeptide consists of amino acids 38 to 654 of SEQ ID NO. 2 or an allelic variant thereof; or a fragment thereof, wherein the fragment has lysophospholipase activity. In another preferred embodiment, the polypeptide consists of amino acids 38 to 654 of SEQ ID NO. 2.

A fragment of SEQ ID NO. 2 is a polypeptide having one or more amino acids deleted from the amino and/or carboxyl terminus of this amino acid sequence. Preferably, a fragment contains at least 500 amino acid residues, more preferably at least 550 amino acid residues, and most preferably at least 600 amino acid residues.

Preferably, the polypeptides of the present invention comprise the amino acid sequence of SEQ ID NO. 16 or an allelic variant thereof; or a fragment thereof that has lysophospholipase activity. In a more preferred embodiment, the polypeptide of the present invention comprise the amino acid sequence of SEQ ID NO. 16. In another preferred embodiment, the polypeptide of the present invention comprises amino acids 17 to 648 of SEQ ID NO. 16, which is the mature polypeptide of SEQ ID NO. 16, or an allelic variant thereof; or a fragment thereof, wherein the fragment has lysophospholipase activity. In another preferred embodiment, the polypeptide of the present invention comprises amino acids 17 to 648 of SEQ ID NO. 16. In another preferred embodiment, the polypeptide of the present invention consists of the amino acid sequence of SEQ ID NO. 16 or an allelic variant thereof; or a fragment thereof, wherein the fragment has lysophospholipase activity. In another preferred embodiment, the polypeptide of the present invention consists of the amino acid sequence of SEQ ID NO. 16. In another preferred embodiment, the polypeptide consists of amino acids 17 to 648 of SEQ ID NO. 16 or an allelic variant thereof; or a fragment thereof, wherein the fragment has lysophospholipase activity. In another preferred embodiment, the polypeptide consists of amino acids 17 to 648 of SEQ ID NO. 16.

A fragment of SEQ ID NO. 16 is a polypeptide having one or more amino acids deleted from the amino and/or carboxyl terminus of this amino acid sequence. Preferably, a fragment contains at least 500 amino acid residues, more preferably at least 550 amino acid residues, and most preferably at least 600 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO. 2 or SEQ ID NO. 16, or the mature polypeptide thereof, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having lysophospholipase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 214 to 2061 of SEQ ID NO. 1 or nucleotides 49 to 1944 of SEQ ID NO. 15, (ii) the genomic DNA sequence containing nucleotides 214 to 2061 of SEQ ID NO. 1 or nucleotides 49 to 1944 of SEQ ID NO. 15, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO. 1 or SEQ ID NO. 15 may be at least 100 nucleotides or preferably at least 200 nucleotides. Moreover, the subsequence may encode a polypeptide fragment which has lysophospholipase activity. The polypeptides may also be allelic variants or fragments of the polypeptides that have lysophospholipase activity.

The nucleic acid sequence of SEQ ID NO. 1 or SEQ ID NO. 15 or a subsequence thereof, as well as the amino acid sequence of SEQ ID NO. 2 or SEQ ID NO. 16, or a fragment thereof, may be used to design a nucleic acid probe to identify and clone DNA encoding polypeptides having lysophospholipase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having lysophospholipase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 1 or SEQ ID NO. 15, or a subsequence thereof, the carrier material is used in a Southern blot. For purposes of the present invention, hybridization indicates that the nucleic acid sequence hybridizes to a nucleic acid probe corresponding to the nucleic acid sequence shown in SEQ ID NO. 1 or SEQ ID NO. 15, its complementary strand, or a subsequence thereof, under low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO. 2, or a subsequence thereof. In another preferred embodiment, the nucleic acid probe is SEQ ID NO. 1. In another preferred embodiment, the nucleic acid probe is nucleotides 214 to 2061 of SEQ ID NO. 1, which encodes a mature polypeptide having lysophospholipase activity. In another preferred embodiment, the nucleic acid probe is the nucleic acid sequence contained in plasmid pFB0346 which is contained in *Escherichia coli* NRRL B-30073, wherein the nucleic acid sequence encodes a polypeptide having lysophospholipase activity. In another preferred embodiment, the nucleic acid probe is the nucleic acid sequence encoding the mature polypeptide coding region contained in plasmid pFB0346 which is contained in *Escherichia coli* NRRL B-30073.

In another preferred embodiment, the nucleic acid probe is a nucleic acid sequence which encodes the polypeptide of SEQ ID NO. 16, or a subsequence thereof. In another preferred embodiment, the nucleic acid probe is SEQ ID NO. 15. In another preferred embodiment, the nucleic acid probe is nucleotides 49 to 1944 of SEQ ID NO. 15, which encodes a mature polypeptide having lysophospholipase activity. In another preferred embodiment, the nucleic acid probe is the nucleic acid sequence contained in *Fusarium verticillioides* CBS 650.96, wherein the nucleic acid sequence encodes a polypeptide having lysophospholipase activity. In another preferred embodiment, the nucleic acid probe is the nucleic acid sequence encoding the mature polypeptide coding region contained in *Fusarium verticillioides* CBS 650.96.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated Tm using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO. 2 or SEQ ID NO. 16, comprising a substitution, deletion, and/or insertion of one or more amino acids.

The amino acid sequences of the variant polypeptides may differ from the amino acid sequence of SEQ ID NO. 2 or SEQ ID NO. 16, or the mature polypeptide thereof, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO. 2 or SEQ ID NO. 16, or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO. 2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis,* Blackwell Scientific Publications, 1973, Chapter 23, or Johnstone and Thorpe, *Immunochemistry in Practice,* Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, A Manual of Quantitative Immunoelectrophoresis, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis,* Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual,* Cold Spring Harbor Press, Cold Spring Harbor, N.Y. .

The polypeptides of the present invention have at least 20%, preferably at least 40%, more preferably at least 60%, even more preferably at least 80%, even more preferably at least 90%, and most preferably at least 100% of the lysophospholipase activity of the mature polypeptide of SEQ ID NO. 2 or SEQ ID NO. 16.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide. A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatuin, Fusarium roseum, Fusarium sambucinum, Fusarium sarcochroum, Fusarium sporotrichioides, Fusarium sulphureum, Fusarium torulosum, Fusarium trichothecioides, Fusarium venenatum,* or *Fusarium verticillioides* polypeptide.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

In a more preferred embodiment, the *Fusarium verticillioides* cell is *Fusarium verticillioides* CBS 650.96.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Fusarium are defined by D. L. Hawksworth, P. M. Kirk, B. C. Sutton, and D. N. Pegler (editors), 1995, *In Ainsworth & Bisby's Dictionary of the Fungi,* Eighth Edition, CAB International, University Press, Cambridge, England, pp. 173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-lysophospholipase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO. 1. In another preferred embodiment, the nucleic acid sequence is set forth in SEQ ID NO. 15. In a more preferred embodiment, the nucleic acid sequence is the sequence contained in plasmid pFB0346 that is contained in *Escherichia coli* NRRL B-30073. In another more preferred embodiment, the nucleic acid sequence is the sequence contained in *Fusarium verticilliodes* CBS 650.96. In another preferred embodiment, the nucleic acid sequence is the mature polypeptide coding region of SEQ ID NO. 1. In another preferred embodiment, the nucleic acid sequence is the mature polypeptide coding region of SEQ ID NO. 15. In another more preferred embodiment, the nucleic acid sequence is the mature polypeptide coding region contained in plasmid pFB0346 that is contained in *Escherichia coli* NRRL B-30073. In another more preferred embodiment, the nucleic acid sequence is the mature polypeptide coding region contained in *Fusarium verticilliodes* CBS 650.96. The present invention also encompasses nucleic acid sequences which encode a polypeptide having the amino acid sequence of SEQ ID NO. 2 or SEQ ID NO. 15, or the mature polypeptide thereof, which differ from SEQ ID NO. 1 or SEQ ID NO. 15, respectively, by virtue of the degeneracy of the genetic code. The present invention also relates to subsequences of SEQ ID NO. 1 or SEQ ID NO. 15, which encode fragments of SEQ ID NO. 2 or SEQ ID NO. 17, respectively, that have lysophospholipase activity.

A subsequence of SEQ ID NO. 1 is a nucleic acid sequence encompassed by SEQ ID NO. 1 except that one or more nucleotides from the 5' and/or 3' end have been deleted.

Preferably, a subsequence contains at least 1500 nucleotides, more preferably at least 1650 nucleotides, and most preferably at least 1800 nucleotides.

A subsequence of SEQ ID NO. 15 is a nucleic acid sequence encompassed by SEQ ID NO. 15 except that one or more nucleotides from the 5' and/or 3' end have been deleted. Preferably, a subsequence contains at least 1500 nucleotides, more preferably at least 1650 nucleotides, and most preferably at least 1800 nucleotides.

The present invention also relates to mutant nucleic acid sequences comprising at least one mutation in the mature polypeptide coding sequence of SEQ ID NO. 1, in which the mutant nucleic acid sequence encodes a polypeptide which consists of amino acids 38 to 654 of SEQ ID NO. 2.

The present invention also relates to mutant nucleic acid sequences comprising at least one mutation in the mature polypeptide coding sequence of SEQ ID NO. 15, in which the mutant nucleic acid sequence encodes a polypeptide which consists of amino acids 17 to 648 of SEQ ID NO. 16.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Fusarium, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO. 1 (i.e., nucleotides 214 to 2061) or SEQ ID NO. 15 (i.e., nucleotides 49 to 1944) of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGNT™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO. 1 or SEQ ID NO. 16, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for lysophospholipase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO. 1 or SEQ ID NO. 16, or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 214 to 2061 of SEQ ID NO. 1 or nucleotides 49 to 1944 of SEQ ID NO. 15, (ii) the genomic DNA sequence containing nucleotides 214 to 2061 of SEQ ID NO. 1 or nucleotides 49 to 1944 of SEQ ID NO. 15, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has lysophospholipase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO. 1 or SEQ ID NO. 15, or a subsequence thereof, wherein the mutant nucleic acid sequence encodes a polypeptide which consists of amino acids 38 to 654 of SEQ ID NO. 2 or amino acids 17 to 648 of SEQ ID NO. 16, or a fragment thereof which has lysophospholipase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptoinyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyL), *Bacillus amyloliquefaciens* alpha-amylase gene (amyQ), *Bacillus licheniformis* penicillinase gene (penP), *Bacillus subtilis* xyla and xylB genes, and prokaryotic beta-lactamase gene (Villa-Kamaroff et al., 1978, *Proceedings of the National Academy of Sciences USA* 75: 3727–3731), as well as the tac promoter (DeBoer et al, 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), Rhizomucor miehei lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharoinyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al, 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide.

Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYCI), and *Saccharoniyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharoinyces cerevisiae* alpha-factor, and *Saccharomyces cerevi-*

*siae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 100 to 150 of SEQ ID NO. 1 which encodes amino acids 1 to 17 of SEQ ID NO. 2.

In a preferred embodiment, the signal peptide coding region is nucleotides 1 to 48 of SEQ ID NO. 15 which encodes amino acids 1 to 16 of SEQ ID NO. 16.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is nucleotides 151 to 213 of SEQ ID NO. 1 which encodes amino acids 18 to 37 of SEQ ID NO. 2.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniform* is, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of *Aspergillus nidulans* or *Aspergillus oryzae* and the bar gene of *Streptoinyces hygroscopicus.*

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB 110, pE 194, pTA1060, and pAMβ1 permitting replication in Bacillus. Examples of origins of replication for use in a yeast host cell are the 2 micron origin of replication, ARS 1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces cell, e.g., *Streptomyces lividans* and *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thome, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell.

In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graininum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum,* or *Fusarium verticillioides* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa,*

*Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Fusarium, and more preferably *Fusarium venenatum* or *Fusarium verticillioides*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO. 1 or SEQ ID NO. 15, wherein the mutant nucleic acid sequence encodes a polypeptide which consists of amino acids 38 to 654 of SEQ ID NO. 2 or amino acids 17 to 648 of SEQ ID NO. 16, respectively, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J. -C. Janson and Lars Ryden, editors, VCH Publishers, New York, 1989).

Plants

The present invention also relates to a transgenic plant, plant part, or plant cell which has been transformed with a nucleic acid sequence encoding a polypeptide having lysophospholipase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and Theological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Vicia faba promoter from the legumin B4 and the unknown seed protein gene from *Vicia faba* (Conrad et al., 1998, *Journal of Plant Physiology* 152: 708–711), a promoter from a seed oil body protein (Chen et al., 1998, *Plant and Cell Physiology* 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having lysophospholipase activity of the present invention under conditions conducive for production of the polypeptide; and (b) recovering the polypeptide.

Removal or Reduction of Lysophospholipase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced lysophospholipase activity may be conveniently accomplished by modification or inactivation of a nucleic acid sequence necessary for expression of the polypeptide having lysophospholipase activity in the cell. The nucleic acid sequence to be modified or inactivated may be, for example, a nucleic acid sequence encoding the polypeptide or a part thereof essential for exhibiting lysophospholipase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the lysophospholipase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced lysophospholipase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of lysophospholipase activity by fermentation of a cell which produces both a polypeptide of the present invention as well as the protein product of interest by adding an effective amount of an agent capable of inhibiting lysophospholipase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of lysophospholipase activity by cultivating the cell under conditions permitting the expression of the product, subjecting the resultant culture broth to a combined pH and temperature treatment so as to reduce the lysophospholipase activity substantially, and recovering the product from the culture broth. Alternatively, the combined pH and temperature treatment may be performed on an enzyme preparation recovered from the culture broth. The combined pH and temperature treatment may optionally be used in combination with a treatment with a lysophospholipase inhibitor.

In accordance with this aspect of the invention, it is possible to remove at least 60%, preferably at least 75%, more preferably at least 85%, still more preferably at least 95%, and most preferably at least 99% of the lysophospholipase activity. Complete removal of lysophospholipase activity may be obtained by use of this method.

The combined pH and temperature treatment is preferably carried out at a pH in the range of 6.5–8.0 and a temperature in the range of 45–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially lysophospholipase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin, glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The lysophospholipase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from lysophospholipase activity which is produced by a method of the present invention.

Uses

The present invention is also directed to methods for using the polypeptides having lysophospholipase activity.

The polypeptides of the present invention may be used in any application where it is desired to hydrolyze the fatty acyl group(s) of a phospholipid or lysophospholipid, such as lecithin or lysolecithin. The polypeptides of the present invention are preferably used at a pH optimal for activity.

A polypeptide having lysophospholipase activity of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269 and EP 808,903.

A polypeptide having lysophospholipase activity of the present invention may be used in a process to reduce the phospholipid content in an edible oil by treating the oil with the polypeptide to hydrolyze a major portion of the phospholipid and separating an aqueous phase containing the hydrolyzed phospholipid from the oil. Such a process is applicable to the purification of any edible oil which contains phospholipid, e.g., vegetable oil such as soybean oil, rape seed oil, and sunflower oil.

Prior to the lysophospholipase treatment, the oil is preferably pretreated to remove slime (mucilage), e.g., by wet refining. Typically, the oil will contain 50–250 ppm of phosphorus as phospholipid at the beginning of the treatment with the lysophospholipase, and the treatment may reduce the phosphorus value to below 5–10 ppm.

The lysophospholipase treatment is conducted by dispersing an aqueous solution of the lysophospholipase, preferably as droplets with an average diameter below 10 $\mu$m. The amount of water is preferably 0.5–5% by weight in relation to the oil. An emulsifier may optionally be added. Mechanical agitation may be applied to maintain the emulsion.

The lysophospholipase treatment can be conducted at a pH in the range of about 1.5 to about 5.0. The process pH may be in the range of about 3.5 to about 5 to maximize the enzyme's performance, or a pH in the range of about 1.5 to about 3 (e.g., 2–3) may be used in order to suppress the alkaline hydrolysis of triglycerides (saponification). The pH may be adjusted by adding citric acid, a citrate buffer, or hydrochloric acid.

A suitable temperature is generally 30–70° C. (particularly 30–45° C., e.g., 35–40° C.). The reaction time will typically be 1–12 hours (e.g., 2–6 hours). A suitable enzyme dosage will usually be 0.1–10 mg per liter (e.g., 0.5–5 mg per liter).

The lysophospholipase treatment may be conducted batchwise, e.g., in a tank with stirring, or it may be continuous, e.g., a series of stirred tank reactors.

The lysophospholipase treatment is followed by separation of an aqueous phase and an oil phase. The separation may be performed by conventional means, e.g., centrifugation. The aqueous phase will contain lysophospholipase, and the enzyme may be re-used to improve the process economy.

The treatment may be performed using any of the methods known in the art. See, for example, U.S. Pat. No. 5,264,367, EP 654,527, JP-A 2-153997.

A polypeptide having lysophospholipase activity of the present invention may be used in the preparation of dough, bread, or cakes. The lysophospholipase is added to the ingredients of a dough which is kneaded and baked to make the bread using methods well known in the art. See, for example, U.S. Pat. No. 4,567,046, EP 426,211, JP-A 60-78529, JP-A 62-111629, and JP-A 63-258528.

The present invention also relates to methods for preparing a dough or a baked product comprising incorporating into the dough an effective amount of a polypeptide of the present invention which improves one or more properties of the dough or the baked product obtained from the dough relative to a dough or a baked product in which the polypeptide is not incorporated.

The phrase "incorporating into the dough" is defined herein as adding the polypeptide having lysophospholipase activity to the dough, any ingredient from which the dough is to be made, and/or any mixture of dough ingredients from which the dough is to be made. In other words, the lysophospholipase may be added in any step of the dough preparation and may be added in one, two, or more steps. The lysophospholipase is added to the ingredients of a dough which is kneaded and baked to make the baked product using methods well known in the art. See, for example, U.S. Pat. No. 4,567,046, EP 426,211, JP-A 60-78529, JP-A 62-111629, and JP-A 63-258528.

The term "effective amount" is defined herein as an amount of the polypeptide having lysophospholipase activity that is sufficient for providing a measurable effect on at least one property of interest of the dough and/or baked product.

The term "improved property" is defined herein as any property of a dough and/or a product obtained from the dough, particularly a baked product, which is improved by the action of the lysophospholipase activity relative to a dough or product in which the polypeptide having lysophospholipase activity is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The improved property may be determined by comparison of a dough and/or a baked product prepared with and without addition of a polypeptide having lysophospholipase activity of the present invention in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved antistaling of the baked product" is defined herein as the properties of a baked product that have a reduced rate of deterioration of quality parameters, e.g., softness and/or elasticity, during storage.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters*.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

The polypeptide having lysophospholipase activity and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme. Granulates and agglomerated powders may be prepared by conventional methods, e.g., by spraying the lysophospholipase onto a carrier in a fluid-bed granulator. The carrier may consist of particulate cores having a suitable particle size. The carrier may be soluble or insoluble, e.g., a salt (such as NaCl or sodium sulfate), sugar (such as sucrose or lactose), sugar alcohol (such as sorbitol), starch, rice, corn grits, or soy. The lysophospholipase and/or additional enzymes may be contained in slow-release formulations. Methods for preparing slow-release formulations are well known in the art. Liquid enzyme preparations may, for instance, be stabilized by adding nutritionally acceptable stabilizers such as a sugar, sugar alcohol, or another polyol, and/or lactic acid or another organic acid according to established methods.

For inclusion in pre-mixes or flour it is advantageous that the polypeptide having lysophospholipase activity is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, lipase (useful for the modification of lipids present in the dough or dough constituents so as to soften the dough), phospholipase (useful for the modification of lipids present in the dough or dough constituents so as to soften the dough and improve gas retention in the dough), cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an aldose oxidase, glucose oxidase, pyranose oxidase, lipoxygenase, or L-amino acid oxidase (useful in improving dough consistency).

When one or more additional enzyme activities are to be added in accordance with the methods of the present invention, these activities may be added separately or together with the polypeptide having lysophospholipase activity, optionally as constituent(s) of the bread-improving and/or dough-improving composition. The other enzyme activities may be any of the enzymes described above and may be dosed in accordance with established baking practices.

The present invention also relates to methods for preparing a baked product, comprising baking a dough obtained by a method of the present invention to produce a baked product. The baking of the dough to produce a baked product may be performed using methods well known in the art.

The present invention also relates to doughs and baked products, respectively, produced by the methods of the present invention. The present invention further relates to a pre-mix, e.g., in the form of a flour composition, for dough and/or baked products made from dough, in which the pre-mix comprises a polypeptide having lysophospholipase activity of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide having lysophospholipase activity of the present invention. The baking additive preferably has a narrow particle size distribution with more than 95% (by weight) of the particles in the range from 25 to 500 $\mu$m.

Signal Peptide and Propeptide

The present invention also relates to nucleic acid constructs comprising a gene encoding a protein operably linked to one or both of a first nucleic acid sequence consisting of nucleotides 100 to 150 of SEQ ID NO. 1 encoding a signal peptide consisting of amino acids 1 to 17 of SEQ ID NO. 2 or nucleotides 1 to 48 of SEQ ID NO. 15 encoding a signal peptide consisting of amino acids 1 to 16 of SEQ ID NO. 16, and a second nucleic acid sequence consisting of nucleotides 151 to 213 of SEQ ID NO. 1 encoding a propeptide consisting of amino acids 18 to 37 of SEQ ID NO. 2, wherein the gene is foreign to the first and second nucleic acid sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first and second nucleic acid sequences may be operably linked to foreign genes individually with other control sequences or in combination with other control sequences.

Such other control sequences are described supra. As noted earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Media and Solutions

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

50×COVE salts solution was composed per liter of 26 g of KCl, 26 g of $MgSO_4.7H_2O$, 76 g of $KH_2PO_4$, and 50 ml of COVE trace metals.

COVE medium was composed per liter of 342.3 g of sucrose, 20 ml of 50×COVE salt solution, 10 ml of 1 M acetamide, 10 ml of 1.5 M $CsCl_2$, and 25 g of Noble agar.

50×Vogels medium was composed per liter of 150 g of sodium citrate, 250 g of $KH_2PO_4$, 10 g of $MgSO_4.7H_2O$, 10 g of $CaCl_2.2H_2O$, 2.5 ml of biotin stock solution, and 5.0 ml of trace metals solution.

Trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

COVE top agarose was composed per liter of 20 ml of 50×COVE salts, 0.8 M sucrose, 1.5 M cesium chloride, 1.0 M acetamide, and 10 g of low melt agarose, pH adjusted to 6.0.

RA sporulation medium was composed per liter of 50 g of succinic acid, 12.1 g of $NaNO_3$, 1 g of glucose, 20 ml of 50×Vogels, and 0.5 ml of a 10 mg/ml $NaMoO_4$ stock solution, pH to 6.0.

YEPG medium was composed per liter of 10 g of yeast extract, 20 g of peptone, and 20 g of glucose.

STC was composed of 0.8 M sorbitol, 25 mM Tris pH 8, 25 mM $CaCl_2$.

SPTC was composed of 40% PEG 4000, 0.8 M sorbitol, 25 mM Tris pH 8, 25 mM $CaCl_2$.

M400Da medium was composed per liter of 50 g of maltodextrin, 2 g of $MgSO_4.7H_2O$, 2 g of $KH_2PO_4$, 4 g of citric acid, 8 g of yeast extract, 2 g of urea, and 1 ml of COVE trace metals solution.

10×basal salts w/o amino acid was composed per liter of 66.8 g of yeast nitrogen base w/o amino acids (Diffco), 100 g of succinic acid, and 60 g of NaOH.

SC Ura-glc medium was composed per liter of 100 ml of 20% glucose, 100 ml of 10×basal salts w/o amino acid, 25 ml of 20% (w/v) casamino acid, 4 ml of 5% of threonine, 10 ml of 1% tryptophan, and 20 g of Agar Noble.

SC Ura-gal medium was composed per liter of 100 ml of 20% galactose, 100 ml of 10×basal salts w/o amino acid, 25 ml of 20% (w/v) casamino acid, 4 ml of 5% of threonine, 10 ml of 1% tryptophan and 20 g of Noble agar.

YPD medium was composed per liter of 10 g of yeast extract, 20 g of bactopeptone, and 100 ml of 20% glucose.

1×TE/LiAc was composed per 10 ml of 1 ml of 10×TE (100 mM of Tris and 10 mM of EDTA at pH), 1 ml of 1 M lithium acetate, and 8 ml of milli Q water.

PEG/LiAc solution was composed of 50 ml of 40% of PEG and 1 ml of 5 M lithium acetate.

Assay plates for detecting lysophospholipase activity were composed per liter of 5 g of L-alpha phosphatidylcholine 95%, 2.5 g of cholic acid, 50 ml of 1 M Tris-HCl pH 8.0 buffer, 100 ml of 100 mM $CaCl_2$, 15 ml of 2% Brilliant green, and 20 g of Agar Noble. The solution was poured into Falcon 1058 plates in 50 ml aliquots.

STET solution was composed of 8% of sucrose, 50 mM Tris-HCl pH 8.0, 50 mM EDTA, and 5% of Triton X-100.

Example 1

Fermentation and Mycelial Tissue

*Fusarium venenatum* CC1-3, a morphological mutant of Fusarium strain ATCC 20334 (Wiebe et al., 1991, *Mycol. Research* 95: 1284–1288), was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 µg of poly(A)+mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP 10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 µg/ml.

Two independent directional cDNA libraries were constructed using the plasmid cloning vector pZErO-2.1. Library A was made using mRNA from mycelia harvested at four days, and Library B was constructed with mRNA from the six day time point. Neither cDNA library was amplified in order to examine a representative "snapshot" of the gene expression profile in the cells. Instead the libraries were plated, titered, and independent clones from each was analyzed by DNA sequencing.

Library A (4 day cells) consisted about $7.5 \times 10^4$ independent clones and Library B (6 day cells) consisted of roughly $1.2 \times 10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg. =1050 bp). Similarly, 39 of 40 colonies (97.5%) picked from Library B had inserts with sizes ranging from 800 bp to 3600 bp (avg. =1380 bp).

Example 3

Template Preparation and Nucleotide Sequencing

From each cDNA library described in Example 2, 1192 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing was done with a Perkin-Elmer Applied Biosystems Model 377 Sequencer XL (Perkin-Elmer Applied Biosystems, Inc., Foster City, Calif.) using dye-terminator chemistry (Giesecke et al., 1992, *Journal of Virology Methods* 38: 47–60) and the reverse lac sequencing primer.

Example 4

Analysis of DNA Sequence Data

Nucleotide sequence data were scrutinized for quality, and samples giving improper spacing or ambiguity levels exceeding 2% were discarded or re-run. Vector sequences were trimmed manually with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to determine multiplicity using AutoAssembler™ software (Perkin-Elmer Applied Biosystems, Inc., Foster City, Calif.). Lastly, all sequences were translated in three frames and searched against a non-redundant database (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of Lysophospholipase cDNA Clone

Putative lysophospholipase clones were identified by partial sequencing of random cDNA clones using an Applied Biosystems Model 377 XL Automated DNA Sequencer according to the manufacturer's instructions and comparison of the deduced amino acid sequence to the amino acid sequence of Penicillium notatum lysophospholipase (Swissprot accession number P39457) as described in Example 4. Among several clones discovered in this manner, one was presumed to be full-length on the basis of its alignment to the *Penicillium notatum* lysophospholipase amino acid sequence and the presence of a possible signal peptide, detected using the Signal-P computer program (Nielsen, et al., 1997, *Protein Engineering* 10: 1–6). This clone designated *E. coli* FB0346 containing pFB0346 was selected for nucleotide sequence analysis and expression studies.

Example 6

Nucleotide Sequencing and Characterization of the *Fusarium venenatum* Lysophospholipase cDNA DNA sequencing was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.). The lysophospholipase clone from *E. coli* FB0346 was sequenced to an average redundancy of 6.9.

The lysophospholipase clone encoded an open reading frame of 1962 bp encoding a polypeptide of 654 amino acids. The nucleotide sequence (SEQ ID NO. 1) and deduced amino acid sequence (SEQ ID NO. 2) are shown in FIGS. 1A, 1B, and 1C. Using the SignalP program (Nielsen et al., 1997, *Protein Engineering* 10: 1–6), a signal peptide of 17 residues was predicted and N-terminal analysis of the secreted protein indicated the presence of a pro region of 20 amino acids (see Example 11), hence indicating a predicted molecular weight of approximately 67 kDa for the secreted lysophospholipase. Thus, the mature lysophospholipase is composed of 617 amino acids.

A comparative alignment of lysophospholipase sequences was undertaken using the Clustal method (Higgins, 1989, *CABIOS* 5: 151–153) using the LASERGENE™ MEGALIGNT™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

The comparative alignment showed that the *Fusarium venenatum* lysophospholipase shares regions of identity with lysophospholipase proteins from *Neurospora crassa* of 59% (TREMBL 042791), *Penicillium notatum* of 52% (Swissprot P39457), *Saccharomyces cerevisiae* of 44% (Swissprot P39105), and *Schizosaccharomyces pombe* of 39% (TREMBL O13857). The identities are highest between regions that are likely to be important for catalytic and/or structural roles of the enzyme. There are 19 potential N-linked glycosylation sites (Asn-X-Ser/Thr) within *Fusarium venenatum* lysophospholipase, and 11 of these are conserved in *Neurospora crassa* lysophospholipase, whereas 10 are conserved in *Penicillium notatum* lysophospholipase. The alignment also indicates the presence of eight Cys residues whose positions are strictly conserved among *Fusarium venenatum, Neurospora crassa, Penicillium notatum, Saccharomyces pombe,* and *Saccharomyces cerevisiae* lysophospholipases.

Example 7

Construction of pDM181

Plasmid pDM181 was constructed using the technique of splice overlap extension to fuse the 1.2 kb *Fusarium oxysporum* trypsin promoter (SP387) to the 1.1 kb *Fusarium oxysporum* trypsin terminator (SP387). A polylinker containing SwaI, KpnI and PacI restriction sites was inserted between the promoter and terminator as part of the overlapping PCR strategy. At the 5' end of the promoter a XhoI site was added and the native EcoRI site was preserved. At the 3' end of the terminator EcoRI, HindIII and NsiI sites were incorporated by the PCR reaction.

A PCR fragment containing −1208 to −1 of the *Fusarium oxysporum* trypsin promoter plus a 25 base pair polylinker was generated from plasmid pJRoy20 (Royer et al., 1995, *Biotechnology* 13: 1479–1483) using the following primers:

```
Primer 1 (sense):
5'-GAGCTCGAGGAATTCTTACAAACCTTCAAC-3'   (SEQ ID NO.3)
      XhoI   EcoRI Primer 2 (antisense):
5'-TTAATTAAGGTACCTGAATTTAAATGGTGAAGAG  (SEQ ID NO.4)
     PacI    KpnI     SwaI
                        ATAGATATCCAAG-3'
```

The 100 μl PCR reaction contained 1×Pwo buffer (Boehringer Mannheim, Indianapolis, Ind.), 200 μM each of dATP, dCTP, dGTP, and dTTP, 10 ng of pJRoy2O, and 5 units of Pwo DNA polymerase (Boehringer Mannheim, Indianapolis, Ind.). PCR conditions used were 95° C. for 3 minutes followed by 25 cycles each at 95° C. for 30 seconds, 50° C. for 1 minute, and 72° C. for 1 minute. The final extension cycle was at 72° C. for 5 minutes.

Using the same PCR conditions, a second PCR fragment containing bp −5 to −1 of the *Fusarium oxysporum* trypsin promoter, a 25 base pair polylinker, and 1060 base pairs of the 3' untranslated region of the *Fusarium oxysporum* trypsin gene (terminator region) was generated from plasmid pJRoy2O using the following primers:

```
Primer 3 (sense):
5'-TCACCATTTAAATTCAGGTACCTTAATTAAATTC  (SEQ ID NO.5)
         SwaI      KpnI    PacI
                     CTTGTTGGAAGCGTCGA-3'

Primer 4 (antisense):
5'-TGGTATGCATAAGCTTGAATTCAGGTAAACAAGA  (SEQ ID NO.6)
       NsiI HindIII EcoRI
                        TATAATTT-3'
```

The final 2.3 kb overlapping PCR fragment which contained −1208 to −1 of the *Fusarium oxysporum* trypsin promoter, the 25 base pair polylinker and 1060 base pairs of the *Fusarium oxysporum* trypsin terminator was obtained using 0.2 μl of the first PCR (promoter) reaction and 3 μl of the second (terminator) reaction as templated and primers 1 and 4. The PCR conditions used were 95° C. for 3 minutes followed by 30 cycles each at 95° C. for 30 seconds, 62° C. for 1 minute, and 72° C. for 3 minutes. The final extension cycle was at 72° C. for 5 minutes. Pwo DNA polymerase was also used for this reaction.

The resulting 2.3 kb fragment containing the trypsin promoter, the polylinker, and the trypsin terminator was digested with EcoRI and ligated into the EcoRI digested vector pMT1612 containing the bar gene (WO 97/26330) to create pDM181 (FIG. 2).

Example 8

Construction of Plasmid pSheB1

Figure 3:
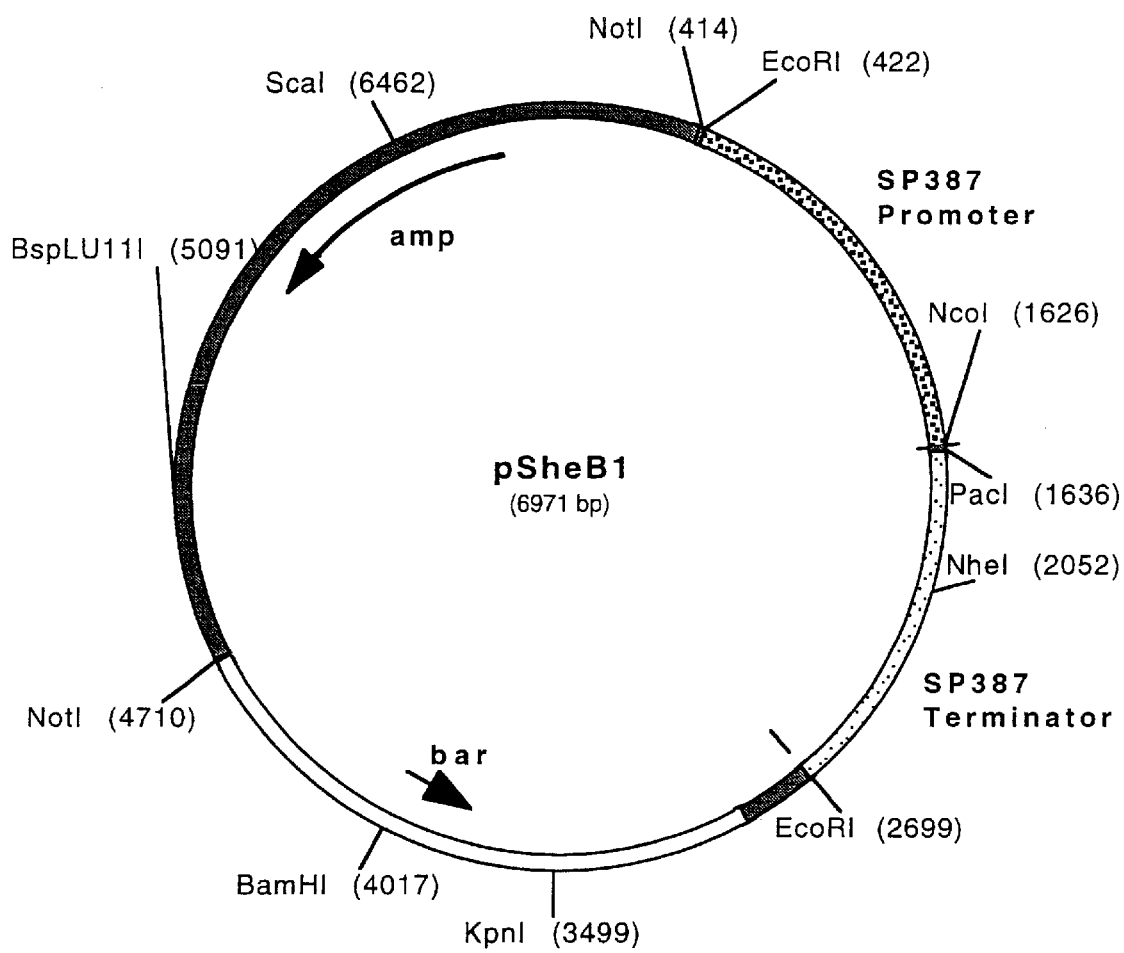
FIG. 3 shows a restriction map of pSheB1.

The *Fusarium venenatum* expression vector pSheB1 (FIG. 3) was generated by modification of pDM181. The modifications included (a) removal of two NcoI sites within the pDM181 sequence, and (b) restoration of the natural translation start of the Fusarium oxysporum trypsin promoter (reconstruction of an NcoI site at the ATG start codon).

Removal of two NcoI sites within the pDM 181 sequence was accomplished using the QuikChange™ site-directed mutagenesis kit (Stratagene Cloning Systems, La Jolla, Calif.) according to the manufacturer's instruction with the following pairs of mutagenesis primers:

5'-dCAGTGAATTGGCCTCGATGGCCGCGGCCGCGA (SEQ ID NO.7)
ATT-3' plus

5'-dAATTCGCGGCCGCGGCCATCGAGGCCAATTCA (SEQ ID NO.8)
CTG-3'

5'-dCACGAAGGAAAGACGATGGCTTTCACGGTGTC (SEQ ID NO.9)
TG-3' plus

5'-dCAGACACCGTGAAAGCCATCGTCTTTCCTTCG (SEQ ID NO.10)
TG-3'

Restoration of the natural translation start of the *Fusarium oxysporum* trypsin promoter was also accomplished using the Stratagene QuikChange™ site directed mutagenesis kit in conjunction with the following pair of mutagenesis primers:

5'-dCTATCTCTTCACCATGGTACCTTAATTAAATA (SEQ ID NO.11)
CCTTGTTGGAAGCG-3' plus

5'-dCGCTTCCAACAAGGTATTTAATTAAGGTACCA (SEQ ID NO.12)
TGGTGAAGAGATAG-3'

All site-directed changes were confirmed by DNA sequence analysis of the appropriate vector regions.

Example 9

Construction of Expression Vector pRaMB54

Figure 4:
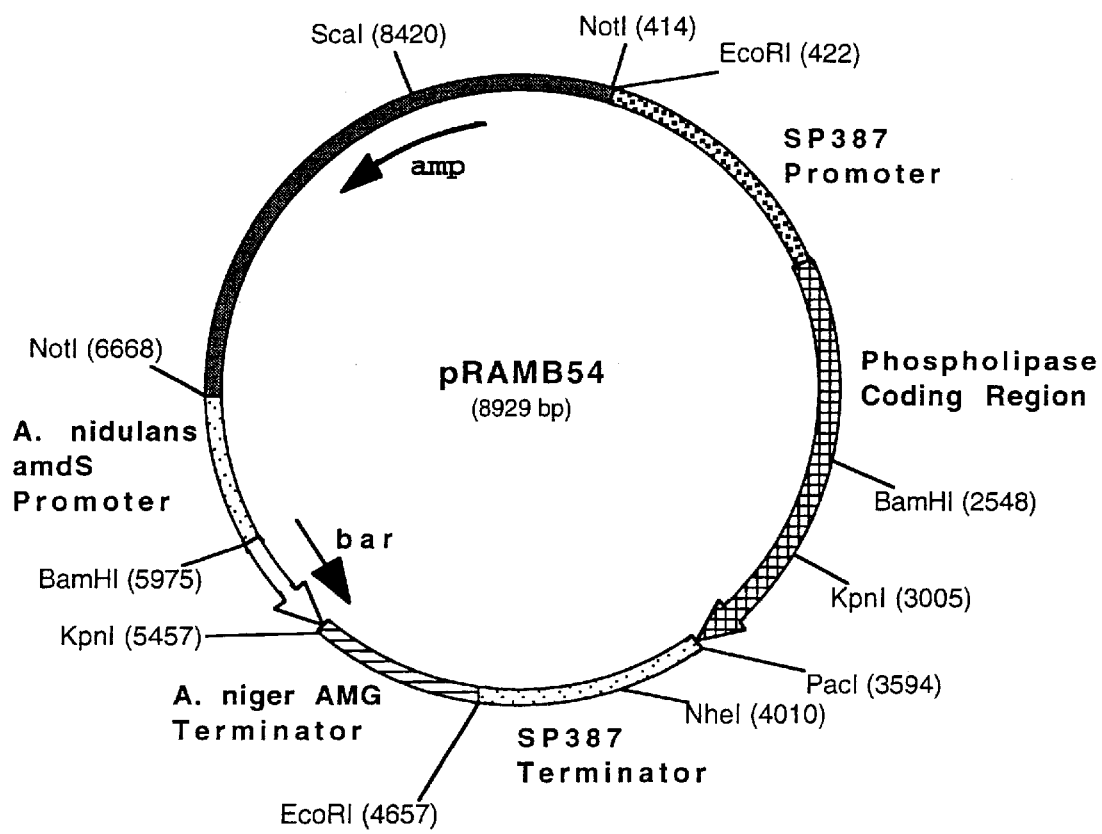
FIG. 4 shows a restriction map of pRaMB54.

The lysophospholipase-expression vector, pRaMB54, was constructed as shown in FIG. 4. The lysophospholipase coding region was amplified from clone FB0346 using the following pair of primers: 5'-dGGCACATGTTGGGCCCTCTCGTCTTTACT-3' (forward) (SEQ ID NO. 13) and 5'-dGACTTAATTAATTTACGAAATAGCCAAGAATA AAGC-3' (reverse) (SEQ ID NO. 14). The forward primer introduces a BspLU11I restriction site at the start codon, and the reverse primer introduces a PacI site after the stop codon.

The amplification reaction (100 µl) contained the following components: 0.8 µg of clone FB0346 cDNA, 40 pmol of the forward primer, 40 pmol of the reverse primer, 200 µM each of dATP, dCTP, dGTP, and dTTP, 1×Pwo DNA polymerase buffer, and 2.5 units of Pwo DNA polymerase. The reactions were incubated in a Perkin-Elmer Model 480 Thermal Cycler programmed for 30 cycles each at 95° C. for 3 minutes, 58° C. for 2 minutes, and 72° C. for 2 minutes. The reaction products were isolated on a 1.5% agarose gel (Eastman Kodak, Rochester, N.Y.) where a 2 kb product band was excised from the gel and purified using Qiaex II (Qiagen, Chatsworth, Calif.) according to the manufacturer's instructions.

The amplified lysophospholipase segment was digested with BspLU11I and PacI, purified by agarose gel electrophoresis using standard methods (Sambrook et al., 1989, supra), and ligated to the vector pSheB1 which had been previously cleaved with NcoI and PacI (note: BspLU11I and NcoI generate compatible cohesive ends). The resulting expression plasmid was designated as pRaMB54.

Example 10

Expression of Lysophospholipase cDNA in *Fusarium venenatum*

Spores of *Fusarium venenatum* CC 1-3 (MLY-3) were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4 \times 10^7$ spores of *Fusarium venenatum* CC 1-3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25 \times 10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* CC1-3 were thawed on ice. Five µg of pRaMB54 described in Example 9 and 5 µl of heparin (5 mg per ml of STC) was added to a 50 ml sterile polypropylene tube. One hundred µl of protoplasts was added, mixed gently, and incubated on ice for 30 minutes. One ml of SPTC was added and incubated 20 minutes at room temperature. After the addition of 25 ml of 40° C. COVE top agarose, the mixture was poured onto an empty 150 mm diameter plate and incubated overnight at room temperature. Then an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Fifteen transformants were picked directly from the selection plates (COVE underlay with COVE-BASTA™ overlay) into 125 ml shake flasks containing 25 ml of M400Da medium supplemented with 1 mM $CaCl_2$ and 100 µg/ml ampicillin (to prevent bacterial contamination) and incubated at 28° C., 200 rpm on a platform shaker for 7 days. The untransformed recipient strain was also included as a negative control.

Flasks were sampled at 5 days. Cells were removed by centrifugation, and 10 µl of each supernatant sample was heated to 95° C. for 5 minutes with an equal volume of SDS-PAGE sample buffer (Novex Experimental Technology, San Diego, Calif.). The denatured supernatant proteins were separated on a 10–20% gradient gel (Novex Experimental Technology, San Diego, Calif.) and stained with Coomassie blue.

Lysophospholipase activity in culture supernatants was also measured using egg yolk lysolecithin as the substrate with a NEFA C assay kit (Wako Chemicals, Richmond, Va.). Specifically, a 10 μl sample of the supernatant was added to 160 μl of 20 mM MOPS pH 7.0 buffer and 30 μl of a stock solution of 5 mg of lysolecithin per ml of 100 mM NaCl and incubated at 37° C. for 20 minutes. Then 20 μl of the reaction was added to 200 μl of Reagent A (Wako Chemicals, Richmond, Va.) and incubated at 37° C. for 10 minutes. Finally, 400 μl of Reagent B (Wako Chemicals, Richmond, Va.) was added and the solution incubated at 37° C. for an additional 10 minutes. The absorbance at 550 nm was measured by transferring 200 μl of the final solution to a 96 well plate and measuring the absorbance with a SpectraMax Model 340 (Molecular Dynamics, Sunnyvale, Calif.) relative to a standard curve constructed with oleic acid as the standard.

The results shown in Table 1 clearly demonstrate the presence of increased lysophospholipase activity in these samples. SDS-PAGE analysis showed that the lysophospholipase-producing transformants secrete a prominent polypeptide with an apparent molecular weight of approximately 116 kDa. The discrepancy between the predicted molecular weight of mature lysophospholipase (ca. 69 kDa) versus that which was observed by SDS-PAGE suggests that the protein is heavily glycosylated. As noted previously, there are 19 potential sites for N-linked glycosylation within the deduced amino acid sequence of *Fusarium venenatum* lysophospholipase.

TABLE 1

Lysophospholipase activity present in culture supernatants from *Fusarium venenatum*/pRaMB54 transformants.

| Transformant | Relative Lysophospholipase Activity[†] |
|---|---|
| RaMB54.01 | 1.00 |
| RaMB54.02 | 0.86 |
| RaMB54.03 | 0.88 |
| RaMB54.04 | 0.88 |
| RaMB54.05 | 0.96 |
| RaMB54.06 | 0.08 |
| RaMB54.10 | 0.85 |
| RaMB54.11 | 0.88 |
| RaMB54.12 | 0.88 |
| RaMB54.14 | 0.35 |
| RaMB54.15 | 1.00 |
| RaMB54.16 | 0.88 |
| RaMB54.17 | 0.88 |
| RaMB54.18 | 0.81 |
| RaMB54.19 | 0.85 |
| MLY-3 control | N.D. |

[†]Activity reflects the rate of hydrolysis of egg yolk lysolecithin at pH 7 and 37° C. measured in micromoles of product per minute per ml relative to the activity of the highest producer RamB54.01 which is normalized to 1.00. N.D., not detected.

Example 11

Purification of Recombinant *Fusarium venenatum* Lysophospholipase

*Fusarium venenatum*/pRaMB54 was cultivated as described in Example 10 for 4 days in two 500 ml shake flasks containing 100 ml of M400Da medium. The 4 day whole culture broths were filtered through Miracloth followed by a 0.45 μm syringe filter (Whatman, Inc., Fairfield, N.J.) to yield a sample volume of approximately 150 ml. Then 25 mM PMSF in 75% ethanol/25% methanol was added to the filtered broth to a final concentration of 0.5 mM. The sample was then diluted with water and 20 mM sodium phosphate pH 7 to achieve a pH of 7.45 and a conductivity of 2.3 mS.

Q-Sepharose Big Beads (Pharmacia Biotech, Inc., Piscataway, N.J.) were prepared in a XK-26 column with a volume of approximately 80 ml of resin. The column had been pre-equilibrated with 500 ml of 20 mM sodium phosphate buffer pH 7.0. The sample was then loaded, followed by washing with 20 mM sodium phosphate pH 7.0 until baseline was achieved. A 600 ml gradient was run from 0 to 0.35 M NaCl at a flow rate of 5 ml/min for 120 minutes. Fractions of 12.5 ml were collected and assayed using lauroyl lysophosphatidylcholine (Sigma Chemical Co., St. Louis, Mo.) as substrate at a concentration of 1.2 mg/ml using the same method described in Example 10. The release of lauric acid was measured using a NEFA C kit. Active fractions were pooled, $(NH_4)_2SO_4$ was added to the pooled fractions to achieve a concentration of 2.2 M, and the pH was adjusted to 7.0 using 1 M NaOH.

The pooled fractions were then loaded onto a Phenyl Superose 16/10 column (Pharmacia Biotech, Inc., Piscataway, N.J.) washed with 100 ml of 50 mM sodium phosphate pH 7.0 and pre-equilibrated with 200 ml of 2.2 M $(NH_4)_2SO_4$ in 50 mM sodium phosphate pH 7.0. The column was then washed with 2.2 M $(NH_4)_2SO_4$ in 50 mM sodium phosphate pH 7.0 buffer until baseline was achieved. Then a 200 ml gradient was run from 2.2 M $(NH_4)_2SO_4$ in 50 mM sodium phosphate pH 7.0 to 50 mM sodium phosphate pH 7.0 containing no $(NH4)_2SO_4$ at a flow rate of 2 ml/min for 100 minutes. Fractions of 4 ml were collected and assayed using the same method described above. Active fractions were also analyzed by SDS PAGE which demonstrated that lysophospholipase was 90–95% pure.

Example 12

Protein Sequencing and Amino Acid Analysis of Recombinant *Fusarium venenatum* Lysophopholipase N-terminal sequencing of a semi-purified lysophospholipase obtained as described in Example 11 and an unpurified lysophospholipase isolated from a broth (5 days) prepared as described in Example 10 was performed on an Applied Biosystems 476A Protein Sequencer (Perkin Elmer/Applied Biosystems Division, Foster City, Calif.) with on-line HPLC and liquid phase trifluoroacetic acid (TFA) delivery. The lysophospholipase preparations were submitted to SDS-PAGE using Novex 8–16% Tris-glycine SDS-PAGE gels under reducing conditions in the presence of 1 mM PMSF. The gels were transblotted to PVDF membranes (Novex, San Diego, Calif.) for 2 hours at 25 volts in 10 mM CAPS pH 11.0 buffer. The PVDF membranes were stained in 0.1% Commassie Blue R250 in 40% methanol/1% acetic acid and the observed bands excised. The excised bands were sequenced from a blot cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software.

SDS-PAGE of the purified lysophospholipase revealed major bands at approximately 130 kDa and 90 kDa, and minor bands at approximately 45, 40, and 35 kDa. Molecular weights were based on pre-stained Multi-Mark SDS page markers which do not reflect accurate MW determinations. N-terminal sequencing of the excised bands produced the following sequences.

```
Run# AB0909 - 130 kDa band sequence:
ALPDSPSGGY.                              (SEQ ID NO.2)

Run# AB0910 - 90 kDa band sequence:
NTAKYWDDIKDTVDEKADGW                     (SEQ ID NO.2)
(Internal peptide following
leucine).

Run# AB0912 - 45 kDa band sequence:
ALPDSPSGGYA                              (SEQ ID NO.2)

Run# AB0913 - 40 kDa band sequence:
ALPDSPSGGYAPKV                           (SEQ ID NO.2)

Run# AB0915 - 35 kDa band sequence:
ALPD(S)P?GGYAP.                          (SEQ ID NO.2)
```

SDS-PAGE of the unpurified lysophospholipase revealed a major band at 116 kDa based on Novex Mark 12 SDS-page markers. N-terminal sequencing of the excised 116 kDa band produced the following sequence:

Run# AB0917–116 kDa band sequence: ALPDSPSG-GYAPKVVD?P (SEQ ID NO. 2) (?=Cys which is undetected without modification in Edman chemistry). The N-terminus appeared to be processed with a 20 amino acid pro-peptide. Cleavage occurred following an arginine.

The overall results are summarized as follows:

```
Signal Sequence: MLGPLVFTLWLTSSAIA       (SEQ ID NO.2)

Pro-peptide:     APDDAGLVAAPAIGKSLSIR    (SEQ ID NO.2)

N-terminus:      ALPDSPSGGYAPKVVDCP      (SEQ ID NO.2)
```

Example 13

Characterization of Recombinant *Fusarium venenatum* Lysophospholipase

The lysophospholipase purified as described in Example 11 was assayed using lysolecithin, dilauroyl L-phosphotidyl choline, and lecithin as substrates. The assay was performed as follows: Lysophospholipase activity in culture supernatants was also measured using egg yolk lysolecithin as the substrate with a NEFA C assay kit (Wako Chemicals, Richmond, Va.). Specifically, a 10 µl sample of the supernatant was added to 160 µl of 20 mM MOPS pH 7.0 buffer and 30 µl of a stock solution of 4 mg of lysolecithin, 5 mg of dilauroyl L-phosphotidyl choline (dispersed by sonication), or 5 mg of lecithin (dispersed by sonication) per ml of 100 mM NaCl and incubated at 37° C. for 20 minutes. Then 20 µl of the reaction was added to 200 µl of Wako Chemicals Reagent A and incubated at 37° C. for 10 minutes. Finally, 400 µl of Wako Chemicals Reagent B was added and the solution incubated at 37° C. for an additional 10 minutes. The absorbance at 550 nm was measured by transferring 200 µl of the final solution to a 96 well plate and measuring the absorbance with a SpectraMax Model 340 relative to a standard curve constructed with oleic acid as the standard. No significant activity was observed with L-phosphatidylcholine and lecithin as substrates.

The pH optimum of the lysophospholipase was determined as follows. Solutions of 0.125 M glycine-acetate-MES-phosphate were prepared at pHs 2,3,4,5,6,7, and 8. A 50 µl volume of a 16 mg/ml solution of lysophosphatidyl choline, lauroyl in 100 mM NaCl was added to 445 µl of the buffer solutions at the different pHs followed by 5 µl of the enzyme solution. After a 5 minute incubation, 1 ml of 5% TCA was added to stop the reaction, followed byl 0.5 ml of hexane and 0.5 ml of ethanol. The solution was vortexed and 500 µl of the hexane layer was removed and added to a conical vial. The hexane was evaporated under nitrogen and the fatty acids were esterified using the Methyl 8 reagent (Pierce, Rockville, Ill.). The resulting samples were the analyzed by gas chromatography using a DB WAX column (length 30 m, I.D. 0.32 mm, film 0.5 µm) (J&W Scientific, Folsom, Calif.) and a temperature gradient from 100 to 200° C. at 4° C. per minute followed by 200 to 270° C. at 35° C. per minute. Detection was by flame ionization. A Grain Fatty Acid Methyl Ester Mix (Supelco, Inc., Bellefonte, Pa.) was used to determine the retention time for lauroyl fatty acid methyl ester and also for quantitation of the fatty acid peaks.

Figure 5:
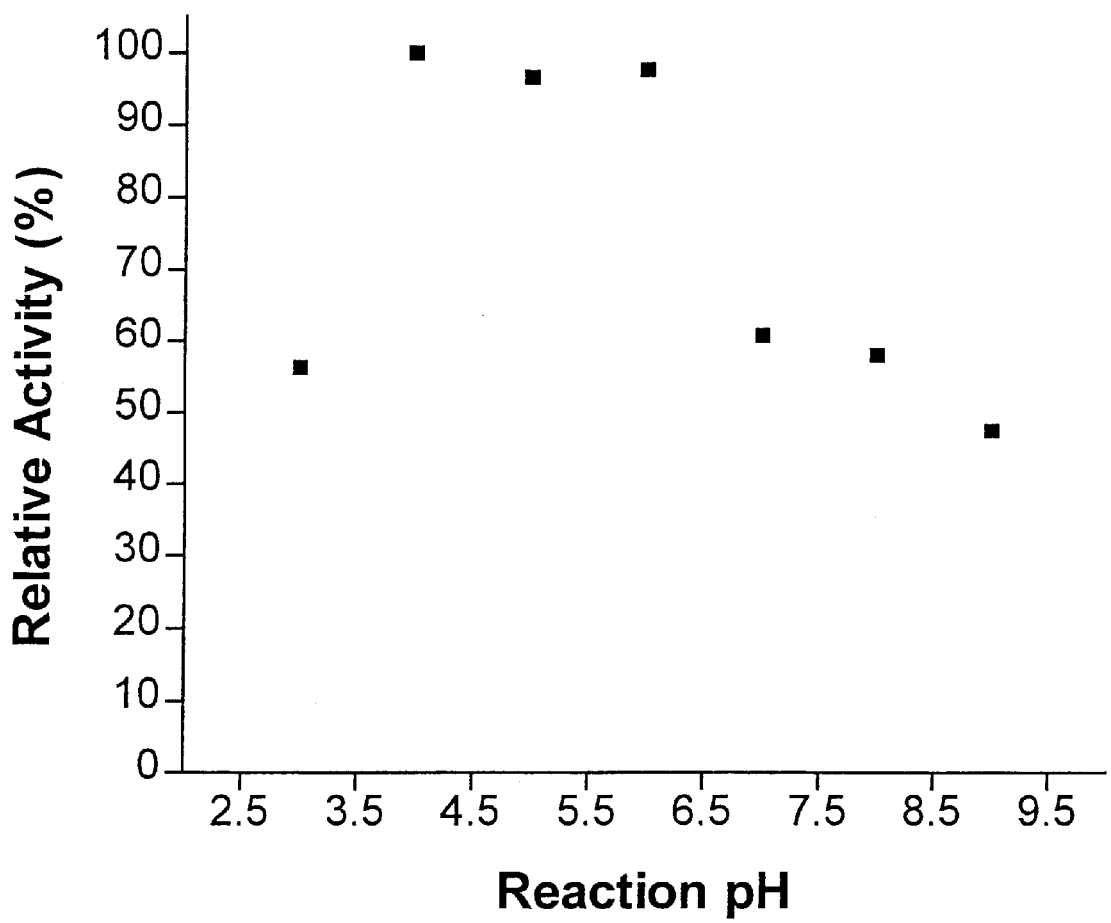
FIG. 5 shows the pH activity profile of a *Fusarium venenatum* lysophospholipase.

The results are shown in FIG. 5. No hydrolysis of the substrate was detected at pH 2 and 8. The pH optimum was determined to be ~4–6.

Example 14

Construction of *Fusarium verticillioides* Lysophospholipase cDNA Library

Mycelia of *Fusarium verticillioides* were prepared similarly as described in Example 1. Poly $A^+$ mRNA was isolated from mycelia of *Fusarium verticillioides* and cDNA was synthesized from the Poly $A^+$ mRNA with BstX1 and NotI linkers similarly as described in Example 2. The cDNA cloned into the yeast expression vector pYES 2.0 (Invitrogen Corporation, Carlsbad, Calif.) according to the manufacturer's instructions.

Example 15

Transformation of *Saccharomyces cerevisiae* with *Fusarium verticillioides* Lysophospholipase cDNA Library Competent cells of *Saccharomyces cerevisiae* YNG318 were prepared using the following procedure. *Saccharoniyces cerevisiae* YNG318 was grown in 20 ml of YPD medium overnight at 30° C. A sufficient seed culture was transferred to 300 ml of YPD medium and cultivated at 30° C. for 3 hours at 230–250 rpm until the $OD_{600}$=0.2–0.3. Then the cells were harvested by centrifugation at 5000 rpm for 5 minutes at 20° C. The pellet was suspended in 50 ml of sterile water and the suspension was centrifuged again. The pellet was then suspended in 1.5 ml of 1×TE/LiAc and glycerol was added to a final concentration of 15%. The competent cells were stored at −80° C. until use.

Transformation of *Saccharomyces cerevisiae* YNG318 was performed with the *Fusarium verticillioides* cDNA library described in Example 14 using the following procedure. A 100 $\mu$l volume of competent cells was thawed on ice and transferred into a sterile tube containing 10 $\mu$l of carrier DNA (yeast marker carrier DNA; Clontech Laboratories, Inc., Palo Alto, Calif.). One $\mu$g of plasmid DNA from Example 14 was added to the tube and the tube was gently mixed. Then 0.6 ml of sterile PEG/LiAc solution was added to the tube. The tube was incubated at 30° C. with shaking at 200 rpm for 30 minutes and then heat-shocked at 42° C. for 15 minutes. After heat-shock the tube was placed on ice and then centrifuged for 5 seconds. The supernatant was removed and the pellet was dissolved in 1.5 ml of YPD. The cells were incubated at 30° C. with shaking at 200 rpm for 45 minutes. The transformants were spread onto sterilized cellulose acetate filters, placed on SC Ura-glc plates, and incubated for 1 day at 30° C. The cellulose acetate filters were transferred onto sterilized Hybond N+ filter, placed onto SC Ura-gal plates, and incubated for 3 days at 30° C.

A total of 89,000 yeast transformants were obtained and screened using the following procedure for expression of lysophospholipase activity. Hybond N+ filters were placed on assay plates and incubated overnight at 30° C. One transformant containing p87YES showed lysophospholipase activity on the assay plate as a green halo.

p87YES was recovered from the yeast transformant using the following procedure. The yeast transformant was grown at 30° C. in 1.5 ml of YPD medium overnight. The cells were harvested by centrifugation and the pellet was re-suspended in 100 μl of STET. A 0.2 g quantity of 0.45 nm glass beads were added and they were mixed with vortex for 5 minutes. Another 100 μl of STET was added and the tube was boiled for 3 minutes. A 100 μl volume of supernatant was transferred to a fresh tube and plasmid DNA was precipitated with ethanol. *E. coli* HB10 was transformed with the precipitated plasmid DNA using standard methods. p87YES was isolated from one of the *E. coli* transformants and sequenced to determine the nucleotide sequence of the *Fusarium verticillioides* lysophospholipase gene.

Example 16

Nucleotide Sequencing and Characterization of the *Fusarium verticillioides* Lysophospholipase cDNA DNA sequencing of p87YES was performed with an ABI PRISM 310 Genetic Analyzer Automated DNA Sequencer using a Dye Terminator Cycle Sequencing FS Ready Reaction Kit according to manufacturer's instructions.

The lysophospholipase clone encoded an open reading frame of 1944 bp encoding a polypeptide of 648 amino acids. The nucleotide sequence (SEQ ID NO. 15) and deduced amino acid sequence (SEQ ID NO. 16) are shown in FIGS. 6A, 6B, and 6C. Using the SignalP program (Nielsen et al., 1997, supra), a signal peptide of 16 residues was predicted. Thus, the mature lysophospholipase is composed of 632 amino acids.

A comparative alignment of lysophospholipase sequences was undertaken using the Clustal method (Higgins, 1989, *CABIOS* 5: 151–153) using the LASERGENE™ MEGALIGNT™ software (DNASTAR, Inc., Madison, Wis.) with an identity table and the following multiple alignment parameters: Gap penalty of 10, and gap length penalty of 10. Pairwise alignment parameters were Ktuple=1, gap penalty= 3, windows=5, and diagonals=5.

The comparative alignment showed that the *Fusarium verticillioides* lysophospholipase shares regions of identity with phospholipase proteins *Neurospora crassa* of 55.4% (042791), *Penicillium notatum* of 49.3% (Swissprot P39457), *Saccharomyces cerevisiae* of 37.0% (EMBL L23089), and *Torulaspora delbrueckii* of 38.3% (EMBL D32134). The identities are highest between regions that are likely to be important for catalytic and/or structural roles of the enzyme.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604, and Centraalbureau voor Schimmelcultures, Oosterstraat 1, P.O. Box 273, 3740 A G Baarn, The Netherlands, and given the following accession numbers:

| Deposit | Accession Number | Date of Deposit |
| --- | --- | --- |
| *E. coli* TOP10 (pFB0346) | NRRL B-30073 | Oct. 27, 1998 |
| *Fusarium verticillioides* | CBS 650.96 | Jun. 5, 1996 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having lysophospholipase activity, selected from the group consisting of:
   (a) an isolated nucleic acid sequence encoding a polypeptide having an amino acid sequence which has at least 80% identity with amino acids 38 to 654 of SEQ ID NO:2 or amino acids 17 to 648 of SEQ ID NO: 16;
   (b) an isolated nucleic acid sequence which hybridizes under medium stringency conditions with (i) nucleotides 214 to 2061 of SEQ ID NO:1 or nucleotides 49 to 1944 of SEQ ID NO:15, (ii) the genomic DNA sequence containing nucleotides 214 to 2061 of SEQ ID NO:1 or nucleotides 49 to 1944 of SEQ ID NO:15, or (iii) a full complementary strand of (i) or (ii); and
   (c) an isolated nucleic acid sequence encoding a polypeptide fragment of (a) or (b), wherein the fragment has lysophospholipase activity.

2. The isolated nucleic acid sequence of claim 1, which encodes a polypeptide having an amino acid sequence which has at least 80% identity with amino acids 38 to 654 of SEQ ID NO:2 or amino acids 17 to 648 of SEQ ID NO:16.

3. The isolated nucleic acid sequence of claim 2, which encodes a polypeptide having an amino acid sequence which has at least 90% identity with amino acids 38 to 654 of SEQ ID NO:2 or amino acids 17 to 648 of SEQ ID NO:16.

4. The isolated nucleic acid sequence of claim 3, which encodes a polypeptide having an amino acid sequence which has at least 95% identity with amino acids 38 to 654 of SEQ ID NO:2 or amino acids 17 to 648 of SEQ ID NO:16.

5. The isolated nucleic acid sequence of claim 4, which encodes a polypeptide having an amino acid sequence which has at least 97% identity with amino acids 38 to 654 of SEQ ID NO:2 or amino acids 17 to 648 of SEQ ID NO:16.

6. The isolated nucleic acid sequence of claim 1, which encodes a polypeptide comprising the amino acid sequence of SEQ ID NO:2 or SEQ ID NO:16.

7. The isolated nucleic acid sequence of claim 1, which encodes a polypeptide consisting of the amino acid sequence of SEQ ID NO:2 or SEQ ID NO:16, or a polypeptide fragment thereof that has lysophospholipase activity.

8. The isolated nucleic acid sequence of claim 7, which encodes a polypeptide consisting of the amino acid sequence of SEQ ID NO:2 or SEQ ID NO:16.

9. The isolated nucleic acid sequence of claim 8, which encodes a polypeptide consisting of amino acids 38 to 654 of SEQ ID NO:2 or amino acids 17 to 648 of SEQ ID NO:16.

10. The isolated nucleic acid sequence of claim 1, which hybridizes under medium stringency conditions with (i) nucleotides 214 to 2061 of SEQ ID NO:1 or nucleotides 49 to 1944 of SEQ ID NO:15, (ii) the genomic DNA sequence containing nucleotides 214 to 2061 of SEQ ID NO:1 or nucleotides 49 to 1944 of SEQ ID NO:15, or (iii) a full complementary strand of (i) or (ii).

11. The isolated nucleic acid sequence of claim 10, which hybridizes under medium-high stringency conditions with (i) nucleotides 214 to 2061 of SEQ ID NO:1 or nucleotides 49 to 1944 of SEQ ID NO:15, (ii) the genomic DNA sequence containing nucleotides 214 to 2061 of SEQ ID NO:1 or nucleotides 49 to 1944 of SEQ ID NO:15, or (iii) a full complementary strand of (i) or (ii).

12. The isolated nucleic acid sequence of claim 11, which hybridizes under high stringency conditions with (i) nucleotides 214 to 2061 of SEQ ID NO:1 or nucleotides 49 to 1944 of SEQ ID NO:15, (ii) the genomic DNA sequence containing nucleotides 214 to 2061 of SEQ ID NO:1 or nucleotides 49 to 1944 of SEQ ID NO:15, or (iii) a full complementary strand of (i) or (ii).

13. The isolated nucleic acid sequence of claim 1, which is contained in plasmid pFB0345 contained in *E. coli* NRRL B-30073.

14. The isolated nucleic acid sequence of claim 1, which is contained in *Fusarium verticillioides* CBS 650.96.

15. The isolated nucleic acid sequence of claim 1, which encodes a polypeptide having at least 20% of the lysophospholipase activity of SEQ ID NO:2 or SEQ ID NO:16.

* * * * *

SEQUENCE LISTING

```
<160> NUMBER OF SEQ ID NOS: 16

<210> SEQ ID NO 1
<211> LENGTH: 2141
<212> TYPE: DNA
<213> ORGANISM: Fusarium venenatum

<400> SEQUENCE: 1
tctacaccta cttgaatagc tatattcccc gacattttat cagcaatatt caagacattc      60
atatcaatac ttagacattg gcttgtttca acaagcaaca tgcttggccc tctcgtcttt     120
actttatggc ttaccagctc ggccattgct gccccggatg acgcgggttt ggtcgcagca     180
ccagcaattg gcaaatccct cagtatccgg gctcttccgg actctccaag cggcggttat     240
gcgccaaaag tggttgactg tccctcgacg cgcccgaaaa tccgacttgc cgatggactt     300
```

```
tcagaccagg aagaagcctg ggttcgtcgc cgaagaaaca acacaataga tccaatgaaa    360
gacttgttat cccgagtcaa catctcgggt ttcgacgccg aaaagtggat tgagaaaaac    420
aaaaacaatg cgactgcgct acctaacatc gccatcgcag cttctggtgg tggataccga    480
gccctcatga acgagcagg cttcatctct gcggctgact cacgcaacaa cgaatccggt     540
cccatcagtg gtcttctaca atcttccact tatttggctg gtctgtcagg aggtggttgg    600
cttgttgggt ctatctttgc caacaacttc accacaatcc ccgacctaca aaagggagac    660
aagggttcag atatctgggc ttttgaccgt tcaattttca aaggacccga aaagtcaggc    720
ttgaacgttt tgaacacggc taaatactgg gatgacataa agacaccgt tgacgaaaag     780
gccgatgggt ggaatactac actcactgac tggtggggtc gtgctctgtc ttaccagctg    840
atcgatgcct ctgagggtgg tcctgcgtat actttctcct ccatcgccga tacttccaac    900
ttcaaggacg ccgatacccc atttcctatc ctcgttgccg atggtcgtgc tcctggtcaa    960
cgcatcgttt cactcaacgc aactgtgtac gagttcaacc cgttcgagtt cggaacatgg   1020
gatcccacta gttacgggtt tgctcccgtc gagtacatcg gctctaactt cacgaatgga   1080
actatcgaaa agggcggcga atgtgtacgt ggctttgatc agttcggctt tgttatgggc   1140
acatcctcct cgttattcaa ccagttcctg ctcaacaaca tcaccaagat tggagaagaa   1200
aatgacattc cttcacttgt cgtgaaggct atccagggat tcctggtagc tttggatacc   1260
aatgatgagg acattgcgga ttattctccc aacccattct accagtggaa cgtgacagga   1320
aaagctaca acgccaagga ccatcaattg actcttgtcg acggagggga ggatctgcag    1380
aatatcccac tccatcccttt gatccagcct gttcgtggtg tcgacatcat ctttgccatc   1440
gattcttcag cggatacgga caacaattgg cccaatggta ccgctcttcg tgcgacatac   1500
gatcgtgtcg attccagctt aggaaacgga actcagtttc cctctattcc atcagctgag   1560
actttcatta atgagaagtt gaaccaacgc ccaacactct ttggctgtga tgcagacaac   1620
ttcacgcttt cagacggcaa agctcctcct cctcttgtct tctacattcc caacgcgccc   1680
tacacattct tgagcaatgt ctctaccttc gatctctcat acagcatccc tgagcgtgac   1740
agtatcattc tcaatgctct gaacggtgcc actcagggca atggtactat tgataaggaa   1800
tggcccacgt gtgtcgtttg tgccatcatg agccgaagtt ggtggaagtc caatgagact   1860
gttcccaaag agtgcagtac gtgtttttgac agatactgct gggacggaaa gtcgaataac   1920
acagctgtta agacttacga gcctggattt atcattgcta acgagactgc ggcggcggaa   1980
gacaatgcag ccgttgccgg tttcacaccg agttggtata tgtctgtgtt tgttggagtg   2040
gctttattct tggctatttc gtaattagca tgtagttct  gagtttgaat atatctacat   2100
catgccaata atataattaa aaaaaaaaaa aaaaaaaaa a                         2141
```

<210> SEQ ID NO 2  
<211> LENGTH: 654  
<212> TYPE: PRT  
<213> ORGANISM: Fusarium venenatum

<400> SEQUENCE: 2

Met Leu Gly Pro Leu Val Phe Thr Leu Trp Leu Thr Ser Ser Ala Ile  
1               5                   10                  15

Ala Ala Pro Asp Asp Ala Gly Leu Val Ala Ala Pro Ala Ile Gly Lys  
            20                  25                  30

Ser Leu Ser Ile Arg Ala Leu Pro Asp Ser Pro Ser Gly Gly Tyr Ala  
        35                  40                  45

```
Pro Lys Val Val Asp Cys Pro Ser Thr Arg Pro Lys Ile Arg Leu Ala
     50                  55                  60

Asp Gly Leu Ser Asp Gln Glu Ala Trp Val Arg Arg Arg Asn
 65              70              75                  80

Asn Thr Ile Asp Pro Met Lys Asp Leu Leu Ser Arg Val Asn Ile Ser
             85                  90                  95

Gly Phe Asp Ala Glu Lys Trp Ile Glu Lys Asn Lys Asn Asn Ala Thr
             100             105             110

Ala Leu Pro Asn Ile Ala Ile Ala Ala Ser Gly Gly Tyr Arg Ala
         115             120             125

Leu Met Asn Gly Ala Gly Phe Ile Ser Ala Ala Asp Ser Arg Asn Asn
     130             135             140

Glu Ser Gly Pro Ile Ser Gly Leu Leu Gln Ser Ser Thr Tyr Leu Ala
145             150             155                     160

Gly Leu Ser Gly Gly Gly Trp Leu Val Gly Ser Ile Phe Ala Asn Asn
             165             170             175

Phe Thr Thr Ile Pro Asp Leu Gln Lys Gly Asp Lys Gly Ser Asp Ile
             180             185             190

Trp Ala Phe Asp Arg Ser Ile Phe Lys Gly Pro Glu Lys Ser Gly Leu
         195             200             205

Asn Val Leu Asn Thr Ala Lys Tyr Trp Asp Asp Ile Lys Asp Thr Val
     210             215             220

Asp Glu Lys Ala Asp Gly Trp Asn Thr Thr Leu Thr Asp Trp Trp Gly
225             230             235             240

Arg Ala Leu Ser Tyr Gln Leu Ile Asp Ala Ser Glu Gly Gly Pro Ala
             245             250             255

Tyr Thr Phe Ser Ser Ile Ala Asp Thr Ser Asn Phe Lys Asp Ala Asp
             260             265             270

Thr Pro Phe Pro Ile Leu Val Ala Asp Gly Arg Ala Pro Gly Gln Arg
         275             280             285

Ile Val Ser Leu Asn Ala Thr Val Tyr Glu Phe Asn Pro Phe Glu Phe
         290             295             300

Gly Thr Trp Asp Pro Thr Ser Tyr Gly Phe Ala Pro Val Glu Tyr Ile
305             310             315             320

Gly Ser Asn Phe Thr Asn Gly Thr Ile Glu Lys Gly Gly Glu Cys Val
             325             330             335

Arg Gly Phe Asp Gln Phe Gly Phe Val Met Gly Thr Ser Ser Ser Leu
             340             345             350

Phe Asn Gln Phe Leu Leu Asn Asn Ile Thr Lys Ile Gly Glu Glu Asn
         355             360             365

Asp Ile Pro Ser Leu Val Val Lys Ala Ile Gln Gly Phe Leu Val Ala
         370             375             380

Leu Asp Thr Asn Asp Glu Asp Ile Ala Asp Tyr Ser Pro Asn Pro Phe
385             390             395             400

Tyr Gln Trp Asn Val Thr Gly Lys Ser Tyr Asn Ala Lys Asp His Gln
             405             410             415

Leu Thr Leu Val Asp Gly Gly Glu Asp Leu Gln Asn Ile Pro Leu His
             420             425             430

Pro Leu Ile Gln Pro Val Arg Gly Val Asp Ile Ile Phe Ala Ile Asp
         435             440             445

Ser Ser Ala Asp Thr Asp Asn Asn Trp Pro Asn Gly Thr Ala Leu Arg
450             455             460
```

Ala Thr Tyr Asp Arg Val Asp Ser Ser Leu Gly Asn Gly Thr Gln Phe
465                 470                 475                 480

Pro Ser Ile Pro Ser Ala Glu Thr Phe Ile Asn Glu Lys Leu Asn Gln
            485                 490                 495

Arg Pro Thr Leu Phe Gly Cys Asp Ala Asp Asn Phe Thr Leu Ser Asp
                500                 505                 510

Gly Lys Ala Pro Pro Leu Val Phe Tyr Ile Pro Asn Ala Pro Tyr
            515                 520                 525

Thr Phe Leu Ser Asn Val Ser Thr Phe Asp Leu Ser Tyr Ser Ile Pro
        530                 535                 540

Glu Arg Asp Ser Ile Ile Leu Asn Ala Leu Asn Gly Ala Thr Gln Gly
545                 550                 555                 560

Asn Gly Thr Ile Asp Lys Glu Trp Pro Thr Cys Val Val Cys Ala Ile
                565                 570                 575

Met Ser Arg Ser Trp Trp Lys Ser Asn Glu Thr Val Pro Lys Glu Cys
            580                 585                 590

Ser Thr Cys Phe Asp Arg Tyr Cys Trp Asp Gly Lys Ser Asn Asn Thr
        595                 600                 605

Ala Val Lys Thr Tyr Glu Pro Gly Phe Ile Ile Ala Asn Glu Thr Ala
610                 615                 620

Ala Ala Glu Asp Asn Ala Ala Val Ala Gly Phe Thr Pro Ser Trp Tyr
625                 630                 635                 640

Met Ser Val Phe Val Gly Val Ala Leu Phe Leu Ala Ile Ser
                645                 650

<210> SEQ ID NO 3
<211> LENGTH: 30
<212> TYPE: DNA
<213> ORGANISM: Fusarium venenatum

<400> SEQUENCE: 3
gagctcgagg aattcttaca aaccttcaac                                    30

<210> SEQ ID NO 4
<211> LENGTH: 47
<212> TYPE: DNA
<213> ORGANISM: Fusarium venenatum

<400> SEQUENCE: 4
ttaattaagg tacctgaatt taaatggtga agagatagat atccaag                 47

<210> SEQ ID NO 5
<211> LENGTH: 51
<212> TYPE: DNA
<213> ORGANISM: Fusarium venenatum

<400> SEQUENCE: 5
tcaccattta aattcaggta ccttaattaa attccttgtt ggaagcgtcg a            51

<210> SEQ ID NO 6
<211> LENGTH: 42
<212> TYPE: DNA
<213> ORGANISM: Fusarium venenatum

<400> SEQUENCE: 6
tggtatgcat aagcttgaat tcaggtaaac aagatataat tt                      42

<210> SEQ ID NO 7
<211> LENGTH: 35

```
<212> TYPE: DNA
<213> ORGANISM: Fusarium venenatum

<400> SEQUENCE: 7
cagtgaattg gcctcgatgg ccgcggccgc gaatt                              35

<210> SEQ ID NO 8
<211> LENGTH: 35
<212> TYPE: DNA
<213> ORGANISM: Fusarium venenatum

<400> SEQUENCE: 8
aattcgcggc cgcggccatc gaggccaatt cactg                              35

<210> SEQ ID NO 9
<211> LENGTH: 34
<212> TYPE: DNA
<213> ORGANISM: Fusarium venenatum

<400> SEQUENCE: 9
cacgaaggaa agacgatggc tttcacggtg tctg                               34

<210> SEQ ID NO 10
<211> LENGTH: 34
<212> TYPE: DNA
<213> ORGANISM: Fusarium venenatum

<400> SEQUENCE: 10
cagacaccgt gaaagccatc gtctttcctt cgtg                               34

<210> SEQ ID NO 11
<211> LENGTH: 46
<212> TYPE: DNA
<213> ORGANISM: Fusarium venenatum

<400> SEQUENCE: 11
ctatctcttc accatggtac cttaattaaa taccttgttg gaagcg                  46

<210> SEQ ID NO 12
<211> LENGTH: 46
<212> TYPE: DNA
<213> ORGANISM: Fusarium venenatum

<400> SEQUENCE: 12
cgcttccaac aaggtattta attaaggtac catggtgaag agatag                  46

<210> SEQ ID NO 13
<211> LENGTH: 29
<212> TYPE: DNA
<213> ORGANISM: Fusarium venenatum

<400> SEQUENCE: 13
ggcacatgtt gggccctctc gtctttact                                     29

<210> SEQ ID NO 14
<211> LENGTH: 36
<212> TYPE: DNA
<213> ORGANISM: Fusarium venenatum

<400> SEQUENCE: 14
gacttaatta atttacgaaa tagccaagaa taaagc                             36

<210> SEQ ID NO 15
```

-continued

<211> LENGTH: 1947
<212> TYPE: DNA
<213> ORGANISM: Fusarium verticillioides

<400> SEQUENCE: 15

```
atgctcggtt ttgtggcctt gacgctctgg ctcagcacag ccattgccgc tccggaagac     60
acggctttga tccccagggt caattcagtc gagatccgag ccctaccaaa ttctccgagt    120
ggcggatatg ctccgaaagt agtcgattgc ccttcaacac gtccaaaagc tcgtcttgcc    180
gatggactgt ctagcgagga agaatcctgg gttcgtcgtc gcagaaacaa cacaatagat    240
gacctaaaga cattcttgtc gcgagccaac atttccggct tcgatgccga gagcttcgtt    300
gagaagcata aaaacaatgc gactggtcta cccaacatcg ccatcgccgc gtccggcggt    360
ggttatcgcg ctttgatgaa cggtgcaggc tttctctcag ctgctgattc acgcaacaac    420
aagaccggcc ccatcagcgg ccttctccag tcagcaacgt atctagctgg tctttctggc    480
ggtggctggc tcgttggttc tattttcgcc aacaatttct caacagtgcc agacttgcaa    540
tctggtgaca aagtctggcg atttgatcgc tccatcttca agggccccaa gagctctgga    600
atcagtctcc tcaacactgc cgagtactgg gatgagatga aagatgccgt tgacgacaag    660
gacaagggct ggaatactac tctcactgat tggtggggcc gcgcattgtc gtatcagctc    720
gtcaatgcgc ctgagggtgg accttcatac actttctctt ccattgccga tacctccaac    780
ttcaaggacg cagacacacc cttccccatc ctcgttgctg atggtcgtgc tccaggtgag    840
cgcgtcatct ccctgaatgc tactgtatac gagttcaacc catacgagtt cggtacatgg    900
gatcctacaa cctttggctt cgtacccact gagtatctcg cttccaactt caccaacggc    960
agcatcagct ccaagggcga atgcgttcgt ggctttgatc agatcggctt tgttatggga   1020
acatcctctt cactattcaa ccagttcctt ctcaacaaca tcaccaaggt cggcaaagag   1080
aatgatattc ccgacattgt tgtcaaagcc attgaaggcg tcttggttgg cttggacgag   1140
gatgatgagg atatcgccca gtatgcaccc aaccccttct tcggatggaa ccctaccgat   1200
aagagcgtca attccaagga ccgccagttg actcttgtcg atggtggaga ggatctgcag   1260
aacattcctc ttcacccatt gatccagccc gttcgtggcg ttgacatcat ttttgccatt   1320
gattcgtctg ctgatacgga caacaactgg cccaatggta ctgctcttcg tgctacatat   1380
gaccgtgttg gttccagcat tggcaacggc acactatttc cctcagtccc atcagctgag   1440
acctttatca acgagaagtt gaaccagcgc cctacgctct ttggctgtaa cgcgaacaac   1500
ttcactcttt cagacggcga agttccccct ccgctgatct tgtacatccc caacgctccc   1560
tacacctacc acagtaacgt ctccaccttc gacatgtcgt ataccactac cgaacgcgac   1620
aacatcattc ttaatgctct caatggagct actcagggta acgctaccat tgacaaggag   1680
tggcctactt gcgtggcgtg tgctgtcatg agcagaagct ggtggaaggc gaatgaggct   1740
gttcctgacg catgcaagac ctgcttcgat cgctactgct gggatggaaa gtctaacaac   1800
actgctgtca agagctatga gcccgagtac atcattggag gaaatgcgac cgcggaagcc   1860
gcagacaacg ctgctggagc caggcttggt ccaagctggt ttgtatcggc tggtgtcggg   1920
gcggctgctt tgtttgctct catgtga                                       1947
```

<210> SEQ ID NO 16
<211> LENGTH: 648
<212> TYPE: PRT
<213> ORGANISM: Fusarium verticillioides

<400> SEQUENCE: 16

-continued

```
Met Leu Gly Phe Val Ala Leu Thr Leu Trp Leu Ser Thr Ala Ile Ala
 1               5                  10                  15
Ala Pro Glu Asp Thr Ala Leu Ile Pro Arg Val Asn Ser Val Glu Ile
            20                  25                  30
Arg Ala Leu Pro Asn Ser Pro Ser Gly Gly Tyr Ala Pro Lys Val Val
            35                  40                  45
Asp Cys Pro Ser Thr Arg Pro Lys Ala Arg Leu Ala Asp Gly Leu Ser
    50                  55                  60
Ser Glu Glu Glu Ser Trp Val Arg Arg Arg Asn Asn Thr Ile Asp
65                  70                  75                  80
Asp Leu Lys Thr Phe Leu Ser Arg Ala Asn Ile Ser Gly Phe Asp Ala
                85                  90                  95
Glu Ser Phe Val Glu Lys His Lys Asn Asn Ala Thr Gly Leu Pro Asn
                100                 105                 110
Ile Ala Ile Ala Ala Ser Gly Gly Gly Tyr Arg Ala Leu Met Asn Gly
                115                 120                 125
Ala Gly Phe Leu Ser Ala Ala Asp Ser Arg Asn Asn Lys Thr Gly Pro
130                 135                 140
Ile Ser Gly Leu Leu Gln Ser Ala Thr Tyr Leu Ala Gly Leu Ser Gly
145                 150                 155                 160
Gly Gly Trp Leu Val Gly Ser Ile Phe Ala Asn Asn Phe Ser Thr Val
                165                 170                 175
Pro Asp Leu Gln Ser Gly Asp Lys Val Trp Arg Phe Asp Arg Ser Ile
                180                 185                 190
Phe Lys Gly Pro Lys Ser Ser Gly Ile Ser Leu Leu Asn Thr Ala Glu
                195                 200                 205
Tyr Trp Asp Glu Met Lys Asp Ala Val Asp Asp Lys Asp Lys Gly Trp
210                 215                 220
Asn Thr Thr Leu Thr Asp Trp Trp Gly Arg Ala Leu Ser Tyr Gln Leu
225                 230                 235                 240
Val Asn Ala Pro Glu Gly Gly Pro Ser Tyr Thr Phe Ser Ser Ile Ala
                245                 250                 255
Asp Thr Ser Asn Phe Lys Asp Ala Asp Thr Pro Phe Pro Ile Leu Val
                260                 265                 270
Ala Asp Gly Arg Ala Pro Gly Glu Arg Val Ile Ser Leu Asn Ala Thr
                275                 280                 285
Val Tyr Glu Phe Asn Pro Tyr Glu Phe Gly Thr Trp Asp Pro Thr Thr
                290                 295                 300
Phe Gly Phe Val Pro Thr Glu Tyr Leu Ala Ser Asn Phe Thr Asn Gly
305                 310                 315                 320
Ser Ile Ser Ser Lys Gly Glu Cys Val Arg Gly Phe Asp Gln Ile Gly
                325                 330                 335
Phe Val Met Gly Thr Ser Ser Leu Phe Asn Gln Phe Leu Leu Asn
                340                 345                 350
Asn Ile Thr Lys Val Gly Lys Glu Asn Asp Ile Pro Asp Ile Val Val
                355                 360                 365
Lys Ala Ile Glu Gly Val Leu Val Gly Leu Asp Glu Asp Asp Glu Asp
370                 375                 380
Ile Ala Gln Tyr Ala Pro Asn Pro Phe Phe Gly Trp Asn Pro Thr Asp
385                 390                 395                 400
Lys Ser Val Asn Ser Lys Asp Arg Gln Leu Thr Leu Val Asp Gly Gly
                405                 410                 415
```

```
Glu Asp Leu Gln Asn Ile Pro Leu His Pro Leu Ile Gln Pro Val Arg
            420                 425                 430

Gly Val Asp Ile Ile Phe Ala Ile Asp Ser Ser Ala Asp Thr Asp Asn
        435                 440                 445

Asn Trp Pro Asn Gly Thr Ala Leu Arg Ala Thr Tyr Asp Arg Val Gly
    450                 455                 460

Ser Ser Ile Gly Asn Gly Thr Leu Phe Pro Ser Val Pro Ser Ala Glu
465                 470                 475                 480

Thr Phe Ile Asn Glu Lys Leu Asn Gln Arg Pro Thr Leu Phe Gly Cys
                485                 490                 495

Asn Ala Asn Asn Phe Thr Leu Ser Asp Gly Glu Val Pro Pro Pro Leu
                500                 505                 510

Ile Leu Tyr Ile Pro Asn Ala Pro Tyr Thr Tyr His Ser Asn Val Ser
            515                 520                 525

Thr Phe Asp Met Ser Tyr Thr Thr Thr Glu Arg Asp Asn Ile Ile Leu
        530                 535                 540

Asn Ala Leu Asn Gly Ala Thr Gln Gly Asn Ala Thr Ile Asp Lys Glu
545                 550                 555                 560

Trp Pro Thr Cys Val Ala Cys Ala Val Met Ser Arg Ser Trp Trp Lys
                565                 570                 575

Ala Asn Glu Ala Val Pro Asp Ala Cys Lys Thr Cys Phe Asp Arg Tyr
            580                 585                 590

Cys Trp Asp Gly Lys Ser Asn Asn Thr Ala Val Lys Ser Tyr Glu Pro
        595                 600                 605

Glu Tyr Ile Ile Gly Gly Asn Ala Thr Ala Glu Ala Ala Asp Asn Ala
    610                 615                 620

Ala Gly Ala Arg Leu Gly Pro Ser Trp Phe Val Ser Ala Gly Val Gly
625                 630                 635                 640

Ala Ala Ala Leu Phe Ala Leu Met
                645
```